US010883118B2

(12) United States Patent
Jessee et al.

(10) Patent No.: US 10,883,118 B2
(45) Date of Patent: *Jan. 5, 2021

(54) AGENTS FOR IMPROVED DELIVERY OF NUCLEIC ACIDS TO EUKARYOTIC CELLS

(71) Applicant: Molecular Transfer Inc., Gaithersburg, MD (US)

(72) Inventors: Joel Jessee, Mount Airy, MD (US); Gulilat Gebeyehu, Potomac, MD (US)

(73) Assignee: Molecular Transfer Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/197,989

(22) Filed: Nov. 21, 2018

(65) Prior Publication Data

US 2019/0264230 A1    Aug. 29, 2019

Related U.S. Application Data

(60) Division of application No. 15/707,740, filed on Sep. 18, 2017, now Pat. No. 10,138,497, which is a division of application No. 14/994,059, filed on Jan. 12, 2016, now Pat. No. 9,765,359, which is a continuation of application No. 14/054,825, filed on Oct. 16, 2013, now Pat. No. 9,259,475, which is a continuation of application No. PCT/US2012/036951, filed on May 8, 2012, which is a continuation of application No. PCT/US2012/033847, filed on Apr. 16, 2012.

(60) Provisional application No. 61/476,240, filed on Apr. 15, 2011.

(51) Int. Cl.
| | |
|---|---|
| C12N 15/88 | (2006.01) |
| A61K 31/195 | (2006.01) |
| C07C 217/08 | (2006.01) |
| A61K 9/127 | (2006.01) |
| A61K 31/713 | (2006.01) |
| C12N 15/113 | (2010.01) |
| C07C 237/10 | (2006.01) |
| C07D 233/64 | (2006.01) |
| C07C 237/12 | (2006.01) |

(52) U.S. Cl.
CPC ............ *C12N 15/88* (2013.01); *A61K 9/1272* (2013.01); *A61K 31/195* (2013.01); *A61K 31/713* (2013.01); *C07C 217/08* (2013.01); *C07C 237/10* (2013.01); *C07C 237/12* (2013.01); *C07D 233/64* (2013.01); *C12N 15/1137* (2013.01); *C12N 2310/14* (2013.01); *C12N 2310/3515* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 5,736,392 | A | 4/1998 | Hawley-Nelson et al. |
| 5,744,625 | A | 4/1998 | Nantz et al. |
| 5,824,812 | A | 10/1998 | Nantz et al. |
| 7,056,704 | B2 | 6/2006 | Tuschl et al. |
| 7,910,363 | B1 | 3/2011 | Phanstiel et al. |
| 9,259,475 | B2 | 2/2016 | Jessee et al. |
| 9,765,359 | B2 | 9/2017 | Jessee et al. |
| 2005/0152964 | A1 | 7/2005 | Huang et al. |
| 2009/0023215 | A1 | 1/2009 | Jessee et al. |
| 2009/0143583 | A1 | 6/2009 | Chu |
| 2010/0260817 | A1 | 10/2010 | Slobodkin et al. |
| 2010/0298403 | A1 | 11/2010 | Tack et al. |

FOREIGN PATENT DOCUMENTS

| | | |
|---|---|---|
| WO | 9610555 A1 | 4/1996 |
| WO | 2007130073 A2 | 11/2007 |

OTHER PUBLICATIONS

International Search Report and Written Opinion for application PCT/US2012/33847; Applicant Molecular Transfer, Inc, dated Aug. 23, 2012; pp. 11.

International Search Report and Written Opinion for application PCT/US2012/36951; Applicant Molecular Transfer, Inc, dated Jul. 13, 2012; pp. 9.

*Primary Examiner* — Richard A Schnizer
(74) *Attorney, Agent, or Firm* — Edell, Shapiro & Finnan, LLC

(57) ABSTRACT

New cationic lipids are provided that are useful for delivering macromolecules, such as nucleic acids, into eukaryotic cells. The lipids can be used alone, in combination with other lipids and/or in combination with other transfection enhancing reagents to prepare transfection complexes.

18 Claims, 4 Drawing Sheets

Specification includes a Sequence Listing.

Figure 1(A)(upper) and 1(B)(lower)
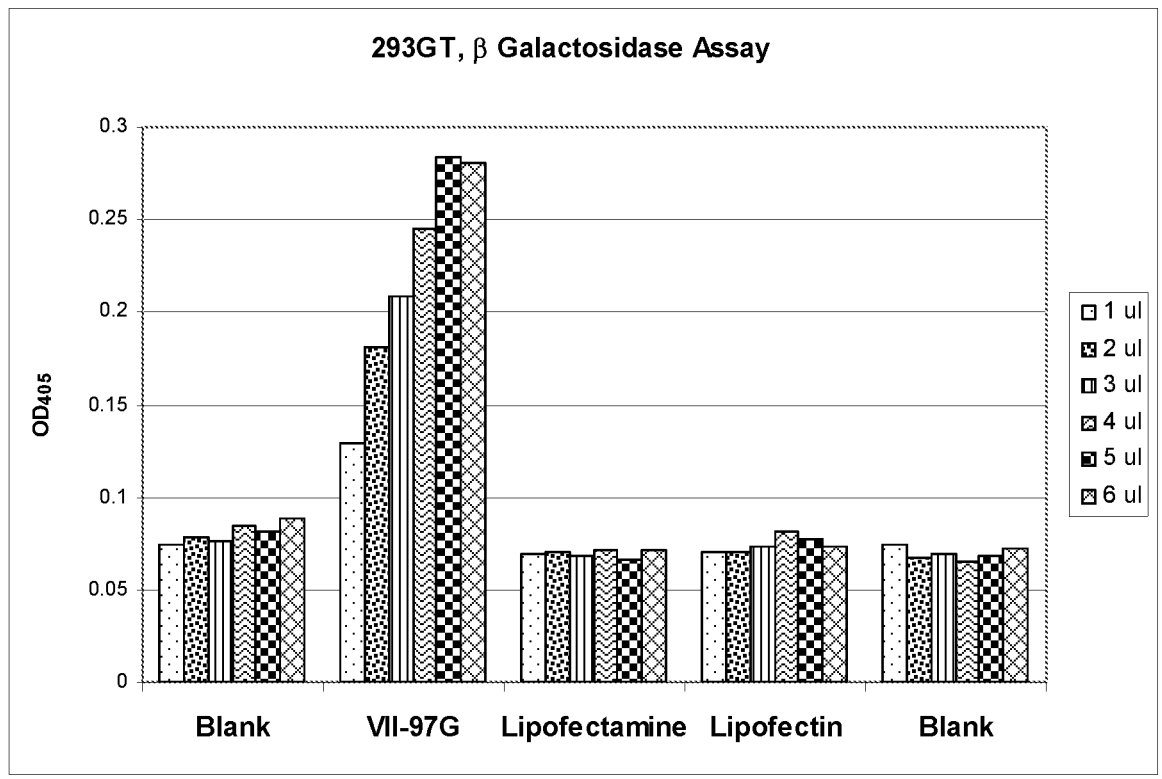
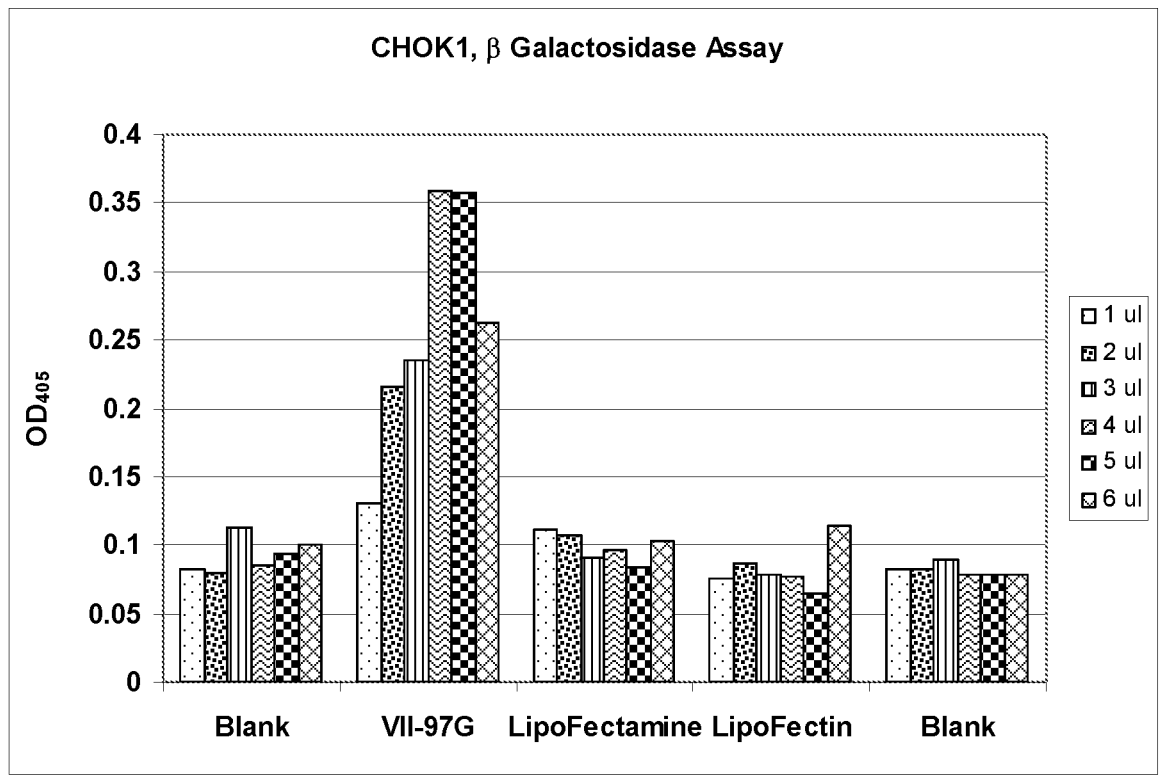

Figure 2(A)(upper) and 2(B)(lower)
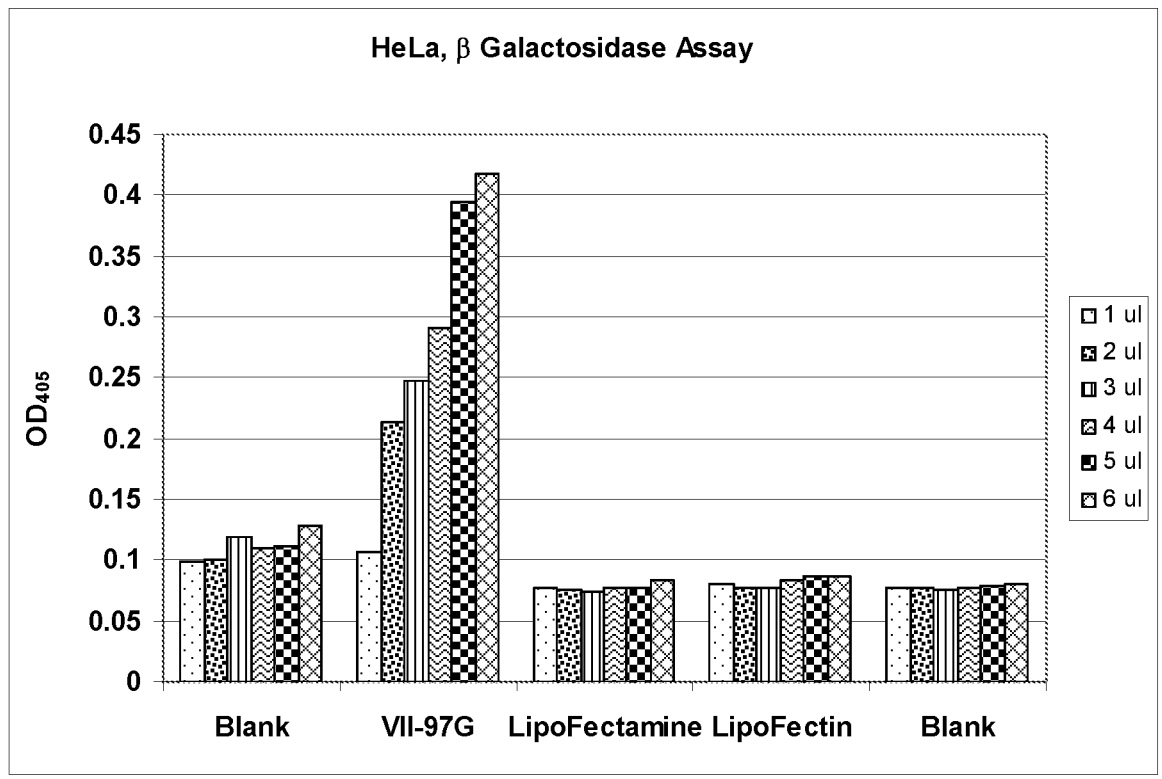
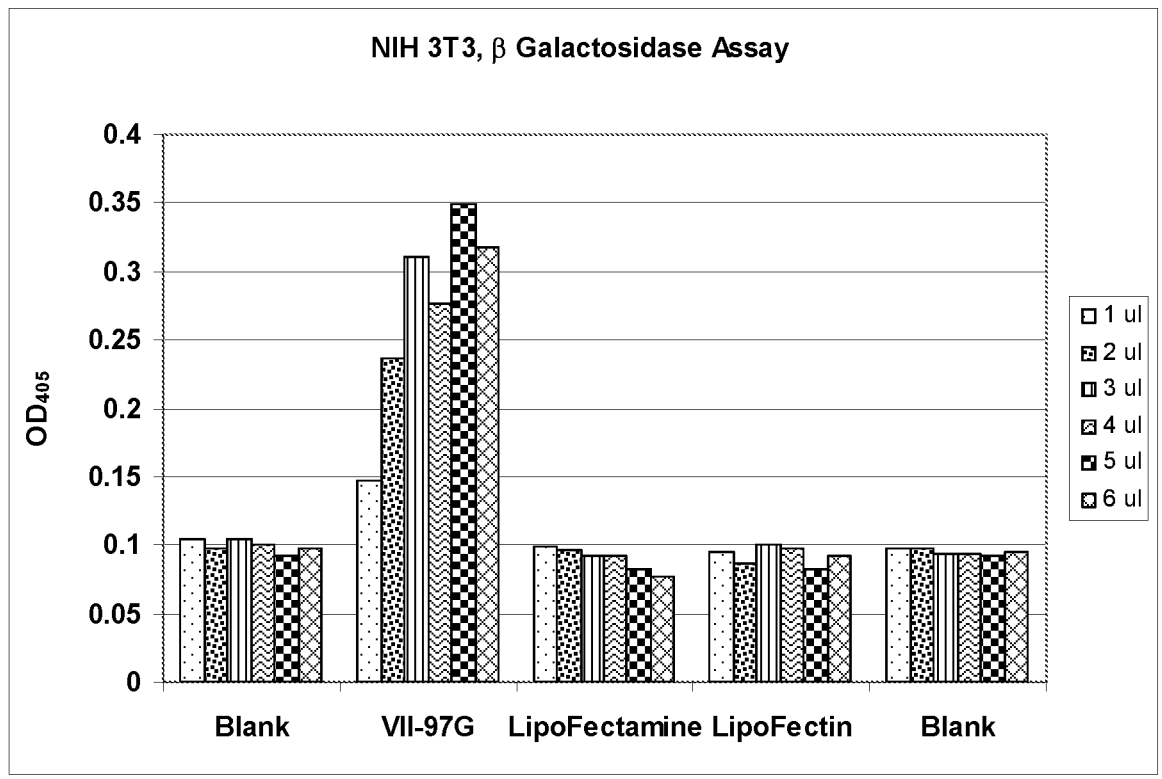

Figure 3(A)(upper) and 3(B)(lower)
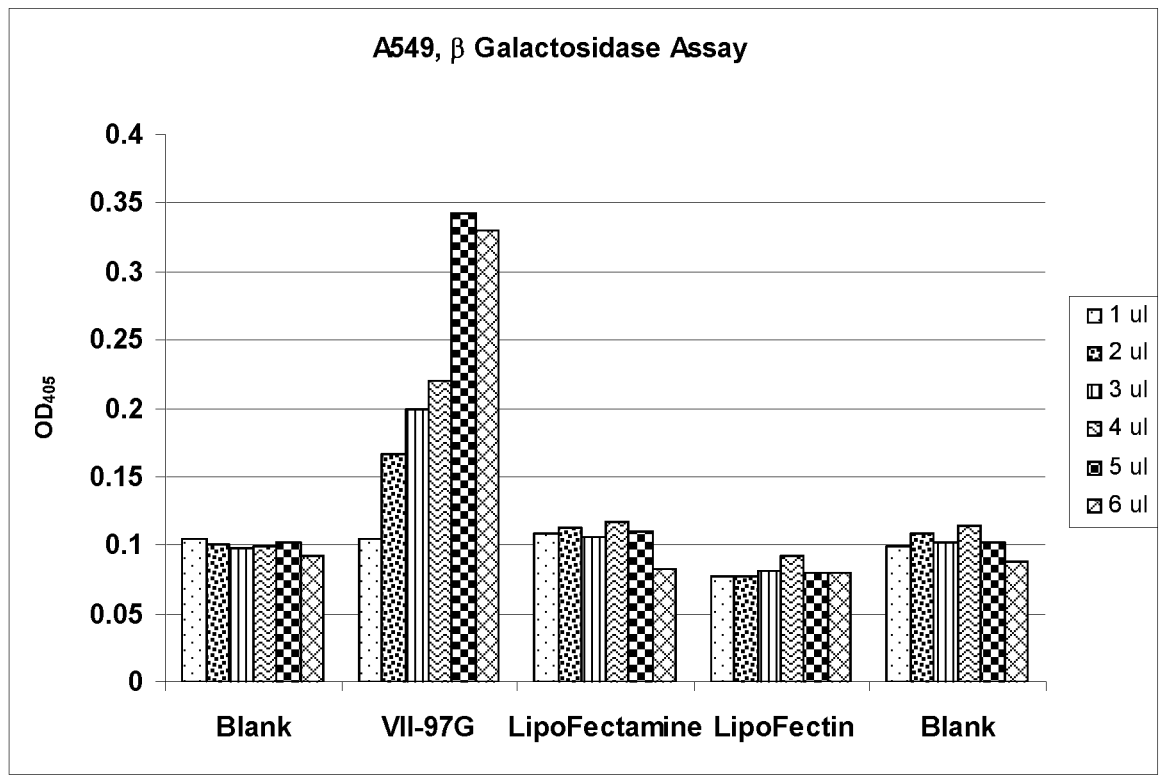
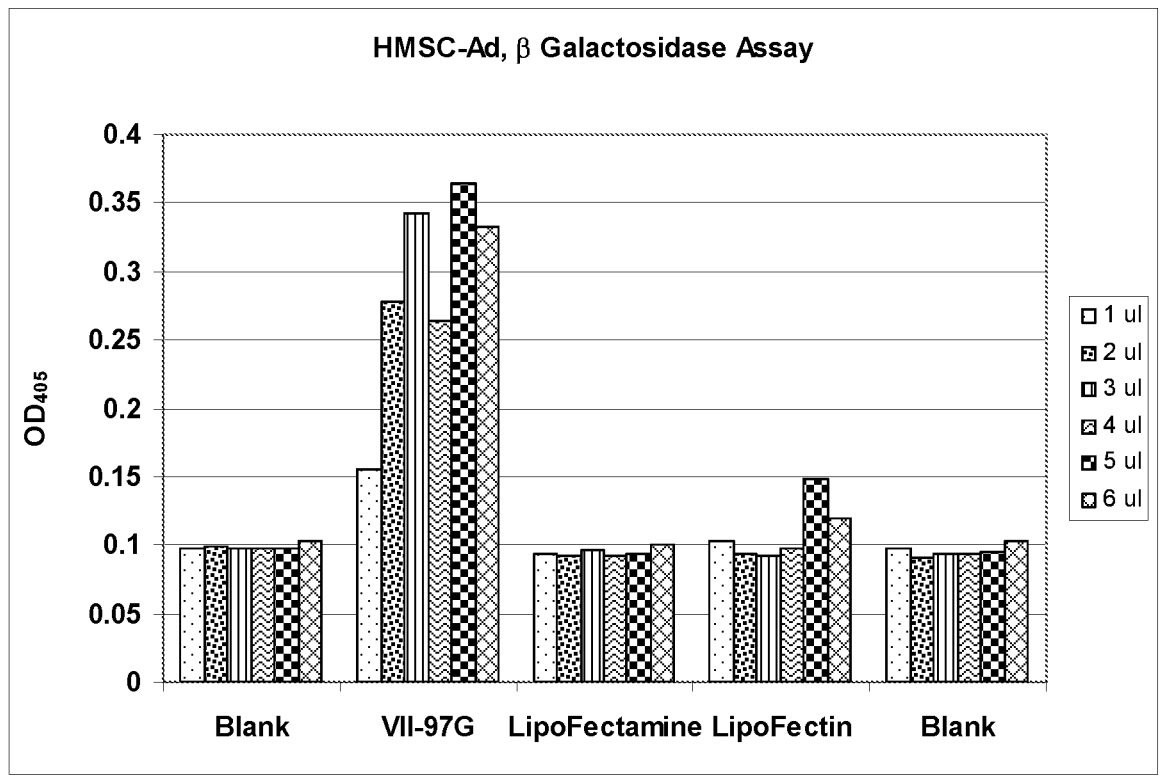

Figure 4(A)(upper) and 4(B)(lower)
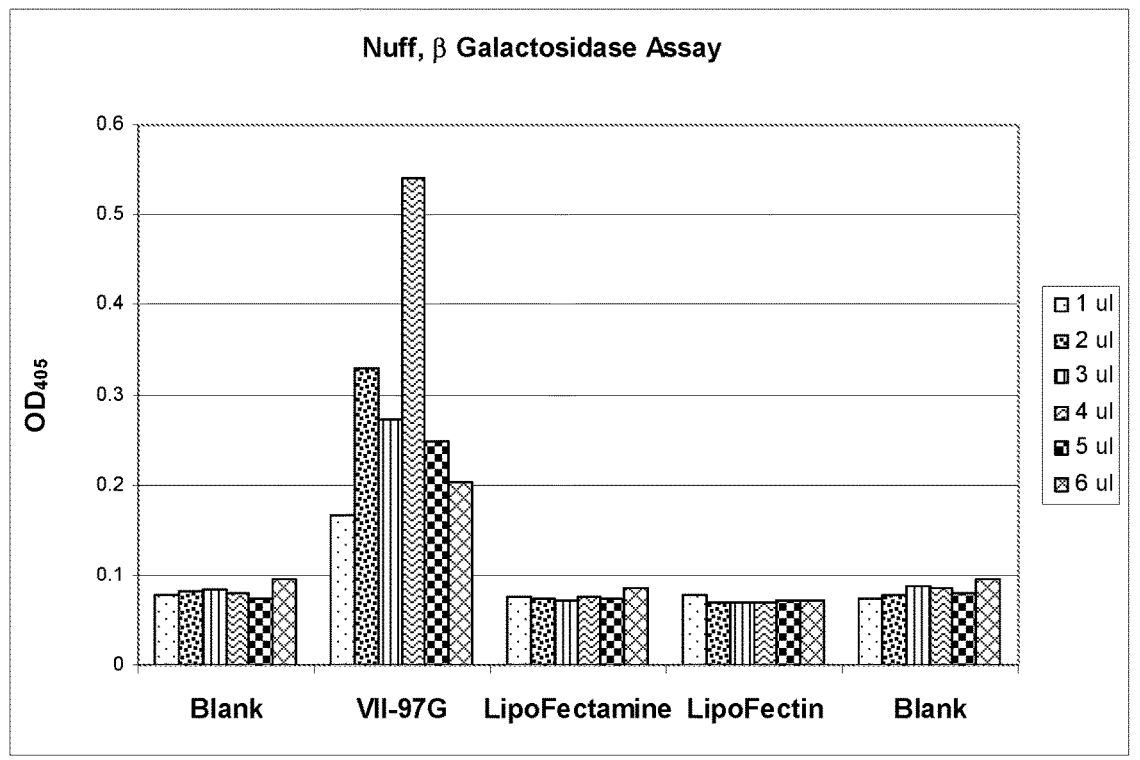
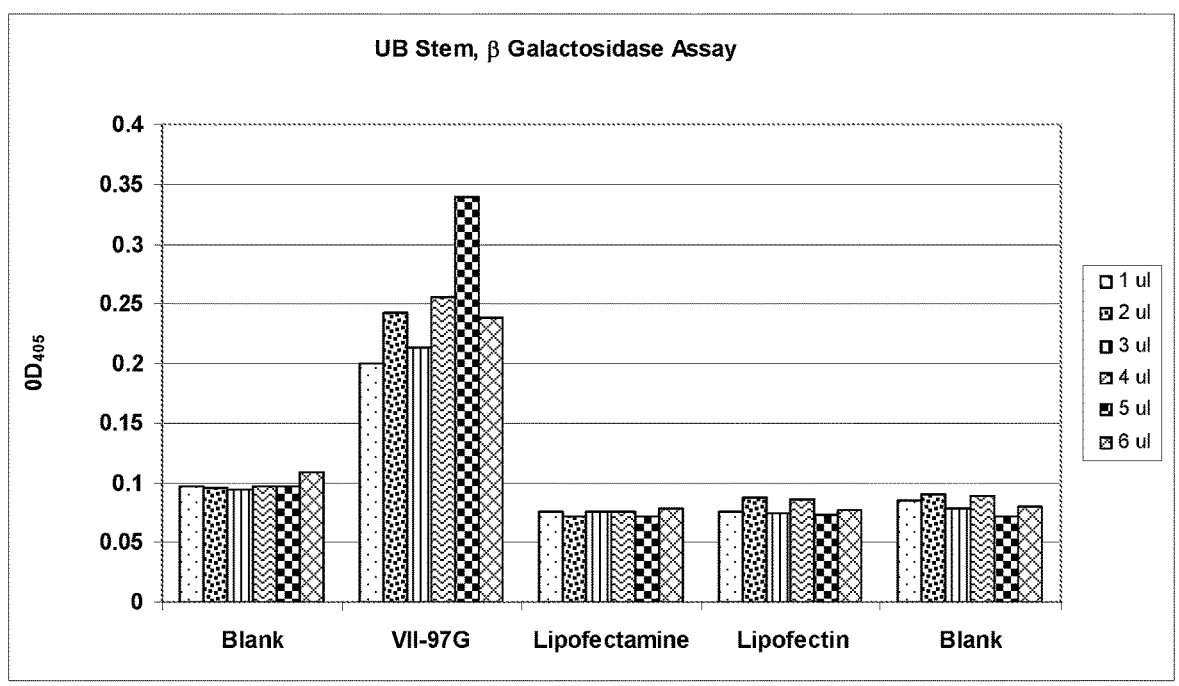

SEQUENCE LISTING

<160> NUMBER OF SEQ ID NOS: 18

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide -continued

```
<400> SEQUENCE: 1

Gly Tyr Ser Thr Pro Pro Lys Lys Arg Lys Val Glu Asp Pro
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: SYNTHETIC PEPTIDE

<400> SEQUENCE: 2

Gly Tyr Ser Thr Pro Pro Lys Thr Arg Arg Arg Pro
1               5                   10

<210> SEQ ID NO 3
<211> LENGTH: 10
<212> TYPE: PRT
<213> ORGANISM: Artificial Sequence
<220> FEATURE:
<223> OTHER INFORMATION: SYNTHETIC PEPTIDE

<400> SEQUENCE: 3

Gly Tyr Ser Thr Pro Gly Arg Lys Lys Arg
1               5                   10

<210> SEQ ID NO 4
<211> LENGTH: 13
<212> TYPE: PRT
<213> ORGANISM: Artificial Sequence
<220> FEATURE:
<223> OTHER INFORMATION: SYNTHETIC PEPTIDE

<400> SEQUENCE: 4

Gly Tyr Ser Thr Pro Arg Arg Asn Arg Arg Arg Arg Trp
1               5                   10

<210> SEQ ID NO 5
<211> LENGTH: 15
<212> TYPE: PRT
<213> ORGANISM: Artificial Sequence
<220> FEATURE:
<223> OTHER INFORMATION: SYNTHETIC PEPTIDE

<400> SEQUENCE: 5

Pro Asp Glu Val Lys Arg Lys Lys Lys Pro Pro Thr Ser Tyr Gly
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: SYNTHETIC PEPTIDE

<400> SEQUENCE: 6

Pro Arg Arg Arg Thr Lys Pro Pro Thr Ser Tyr Gly
1               5                   10

<210> SEQ ID NO 7
<211> LENGTH: 10
<212> TYPE: PRT
<213> ORGANISM: Artificial Sequence
<220> FEATURE:
<223> OTHER INFORMATION: SYNTHETIC PEPTIDE

<400> SEQUENCE: 7
```

```
Arg Lys Lys Arg Gly Pro Thr Ser Tyr Gly
1               5                   10

<210> SEQ ID NO 8
<211> LENGTH: 13
<212> TYPE: PRT
<213> ORGANISM: Artificial Sequence
<220> FEATURE:
<223> OTHER INFORMATION: SYNTHETIC PEPTIDE

<400> SEQUENCE: 8

Trp Arg Arg Arg Arg Asn Arg Arg Pro Thr Ser Tyr Gly
1               5                   10

<210> SEQ ID NO 9
<211> LENGTH: 38
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: REPEAT
<222> LOCATION: (37)..(37)
<223> OTHER INFORMATION: Xaa is from 1-21 lysine residues
<220> FEATURE:
<221> NAME/KEY: REPEAT
<222> LOCATION: (37)..(37)
<223> OTHER INFORMATION: Xaa is from 1-20 lysine residues

<400> SEQUENCE: 9

Gly Tyr Gly Pro Pro Lys Lys Arg Lys Val Glu Ala Pro Tyr Lys
1               5                   10                  15

Ala Lys Lys Lys Lys Lys Lys Lys Lys Lys Lys Lys Lys Lys Lys
            20                  25                  30

Lys Lys Lys Lys Xaa Lys
            35

<210> SEQ ID NO 10
<211> LENGTH: 14
<212> TYPE: PRT
<213> ORGANISM: Artificial Sequence
<220> FEATURE:
<223> OTHER INFORMATION: SYNTHETIC PEPTIDE

<400> SEQUENCE: 10

Phe Glu Ala Ala Leu Ala Glu Ala Leu Ala Glu Ala Leu Ala
1               5                   10

<210> SEQ ID NO 11
<211> LENGTH: 12
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: ACETYLATION

<400> SEQUENCE: 11

Leu Ala Arg Leu Leu Pro Arg Leu Leu Ala Arg Leu
1               5                   10
```

```
<210> SEQ ID NO 12
<211> LENGTH: 20
<212> TYPE: PRT
<213> ORGANISM: Artificial Sequence
<220> FEATURE:
<223> OTHER INFORMATION: SYNTHETIC PEPTIDE

<400> SEQUENCE: 12

Gly Leu Leu Glu Glu Leu Leu Glu Leu Leu Glu Glu Leu Trp Glu Glu
1               5                   10                  15

Leu Leu Glu Gly
            20

<210> SEQ ID NO 13
<211> LENGTH: 19
<212> TYPE: PRT
<213> ORGANISM: Artificial Sequence
<220> FEATURE:
<223> OTHER INFORMATION: SYNTHETIC PEPTIDE

<400> SEQUENCE: 13

Gly Trp Glu Gly Leu Ile Glu Gly Ile Glu Gly Gly Trp Glu Gly Leu
1               5                   10                  15

Ile Glu Gly

<210> SEQ ID NO 14
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 14

Gly Leu Phe Glu Ala Leu Ala Glu Phe Ile Glu Gly Gly Trp Glu Gly
1               5                   10                  15

Leu Ile Glu Gly
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 15

Gly Leu Phe Glu Ala Leu Leu Glu Leu Leu Glu Ser Leu Trp Glu Leu
1               5                   10                  15

Leu Leu Glu Ala
            20

<210> SEQ ID NO 16
<211> LENGTH: 22
<212> TYPE: PRT
<213> ORGANISM: Artificial Sequence
<220> FEATURE:
<223> OTHER INFORMATION: SYNTHETIC PEPTIDE

<400> SEQUENCE: 16

Gly Gly Tyr Cys Leu Glu Lys Trp Met Ile Val Ala Ser Glu Leu Lys
1               5                   10                  15

Cys Phe Gly Asn Thr Ala
            20
```

```
<210> SEQ ID NO 17
<211> LENGTH: 23
<212> TYPE: PRT
<213> ORGANISM: Artificial Sequence
<220> FEATURE:
<223> OTHER INFORMATION: SYNTHETIC PEPTIDE

<400> SEQUENCE: 17

Gly Gly Tyr Cys Leu Thr Arg Trp Met Leu Ile Glu Ala Glu Leu Lys
1               5                   10                  15

Cys Phe Gly Asn Thr Ala Val
            20

<210> SEQ ID NO 18
<211> LENGTH: 30
<212> TYPE: PRT
<213> ORGANISM: Artificial Sequence
<220> FEATURE:
<223> OTHER INFORMATION: SYNTHETIC PEPTIDE

<400> SEQUENCE: 18

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30
```

AGENTS FOR IMPROVED DELIVERY OF NUCLEIC ACIDS TO EUKARYOTIC CELLS

This application is a divisional of U.S. patent application Ser. No. 15/707,740, filed Sep. 18, 2017, which is a divisional of U.S. patent application Ser. No. 14/994,059, filed Jan. 12, 2016, now U.S. Pat. No. 9,765,359, which is a continuation of U.S. patent application Ser. No. 14/054,825, filed Oct. 16, 2013, now U.S. Pat. No. 9,259,475, which is a continuation of PCT Application No PCT/US2012/036951, filed May 8, 2012, which is a continuation-in-part of PCT application PCT/US12/33847, filed Apr. 16, 2012, which claims the benefit of U.S. Provisional Application No. 61/476,240, filed Apr. 15, 2011, the contents of each of which are incorporated herein by reference in their entireties. This application also contains a sequence listing submitted electronically via EFS-web, which serves as both the paper copy and the computer readable form (CRF) and consists of a file entitled "Sequence_Listing_3955_0006DIV.txt", which was created on Sep. 18, 2017, which is 5,549 bytes in size, and which is herein incorporated by reference in its entirety.

BACKGROUND

Transfection agents, such as lipid aggregates comprising cationic lipid components have been used to deliver large anionic molecules, such as nucleic acids, into certain types of cells. See Felgner et al., Nature 337:387-388 (1989); Proc. Natl. Acad. Sci. USA 84:7413 (1987). These agents are not, however, universally effective in all cell types. In many cases, cationic lipids alone are not effective or are only partially effective for transfection. Moreover, these methods do not work for all cell types, often require relatively complex protocols and are inconvenient. It is apparent, therefore, that new and improved methods for introducing macromolecules, and particularly nucleic acids, into cell, are greatly to be desired. In particular, improved methods for introducing nucleic acids into a wider variety of cells, and particularly into primary cells, are greatly to be desired.

SUMMARY OF THE INVENTION

New compounds, compositions and methods are provided that improve the efficiency of introducing macromolecules, such as nucleic acids, into cells. New cationic lipid molecules are provided, together with compositions containing those lipids and methods for using the new lipid molecules and compositions for transfection. The cationic lipids may be used alone for transfection, or they may be used in combination with additional reagents in transfection compositions. For example, the cationic lipids may be combined with one or more neutral lipids, additional cationic lipids, one or more cell surface ligands, one or more fusion enhancing agents, and/or one or more nuclear localization agents. The resulting compositions may be complexed with one or macromolecules, such as DNA or RNA and used to deliver the macromolecule into eukaryotic cells.

Specifically there is provided a compound having the structure (I)

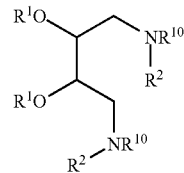

where each $R^1$ independently is $C_1$-$C_{23}$ alkyl, $C_1$-$C_{23}$ alkenyl, —(CO)$C_1$-$C_{23}$ alkyl, or (CO)$C_1$-$C_{23}$ alkenyl; and each $R^2$ independently is —CH$_2$—(CHR$^3$)$_{1-6}$—CH$_2$—NHR$^4$ or CH$_2$—(CHR$^3$)$_{0-6}$—CH$_2$—OH, where each $R^3$ independently is H, OH, or NH$_2$, $R^4$ is H or CH$_3$; and $R^{10}$ is H or $C_1$-$C_8$ alkyl.

In one embodiment, $R^1$ may be $C_{14}$-$C_{20}$ alkyl or monounsaturated $C_{14}$-$C_{20}$-alkenyl. In this and other embodiments, $R^2$ may be —CH$_2$—(CHR$^3$)$_{1-6}$—CH$_2$—NHR$^4$ and $R^3$ is H or OH. In some embodiments, no more than 3 $R^3$ groups are OH in each $R^3$ moiety.

In any of these embodiments, each $R^1$ may be the same or different, and each $R^2$ may be the same or different. In specific embodiments, one or both $R^{10}$ may be H, or one or both $R^{10}$ may be $C_1$-$C_3$ alkyl, for example, one or both $R^{10}$ may be methyl.

In particular embodiment above, one or both $R^1$ may be $C_{12}$-$C_{20}$ alkenyl, and the alkenyl moieties may be cis alkenyl.

In specific embodiments, one or both $R^2$ may be —CH$_2$—CHOH—(CHR$^3$)$_{0-5}$—CH$_2$—NHR$^4$; for example one or both $R^2$ may be —CH$_2$—CHOH—CH$_2$—NH$_2$.

Also provided are compositions containing a compound as described above and at least one cationic lipid, and/or at least one neutral lipid. The cationic lipid may be LipofectAmine™ 2000, LipofectAmine™, Lipofectin®, DMRIE-C, CellFectin® (Invitrogen), Oligofectamine® (Invitrogen), LipofectAce® (Invitrogen), Fugene® (Roche, Basel, Switzerland), Fugene® HD (Roche), Transfectam® (Transfectam, Promega, Madison, Wis.), Tfx-10® (Promega), Tfx-20® (Promega), Tfx-50® (Promega), Transfectin™ (BioRad, Hercules, Calif.), SilentFect™ (Bio-Rad), Effectene® (Qiagen, Valencia, Calif.), DC-chol (Avanti Polar Lipids), GenePorter® (Gene Therapy Systems, San Diego, Calif.), DharmaFect 1® (Dharmacon, Lafayette, Colo.), DharmaFect 2® (Dharmacon), DharmaFect 3® (Dharmacon), DharmaFect 4® (Dharmacon), Escort™ III (Sigma, St. Louis, Mo.), Escort™ IV (Sigma), DOTMA, DOTAP, DMRIE, DC-Chol, DDAB, DOSPA, DOSPER, DOGS, TMTPS, TMTOS, TMTLS, TMTMS, TMDOS, N-1-dimethyl-N-1-(2,3-diaoleoyloxypropyl)-2-hydroxypropane-1,3-diamine, N-1-dimethyl-N-1-(2,3-diamyristyloxypropyl)-2-hydroxypropane-1,3-diamine, N-1-dimethyl-N-1-(2,3-diapalmityloxypropyl)-2-hydroxypropane-1,3-diamine, N-1-dimethyl-N-1-(2,3-diaoleoyloxypropyl)-2-(3-amino-2-hydroxypropyloxy)propane-1,3-diamine, N-1-dimethyl-N-1-(2,3-diamyristyloxypropyl)-2-(3-amino-2-hydroxypropyloxy)propane-1,3-diamine, N-1-dimethyl-N-1-(2,3-diapalmityloxypropyl)-2-(3-amino-2-hydroxypropyloxy)propane-1,3-diamine, L-spermine-5-carboxyl-3-(DL-1,2-dipalmitoyl-dimethylaminopropyl-β-hydroxyethylamine, 3,5-(N,N-dilysyl)-diaminobenzoyl-glycyl-3-(DL-1,2-dipalmitoyl-dimethylaminopropyl-(3-hydroxyethylamine), L-Lysine-bis(O,O'-oleoyl-β-hydroxyethyl)amide dihydrochloride, L-Lysine-bis-(O,O'-palmitoyl-β-hydroxyethyl)amide dihydrochloride, 1,4-bis [(3-(3-aminopropyl)-alkylamino)-2-hydroxypropyl)]

piperazine, L-Lysine-bis-(O,O'-myristoyl-β-hydroxyethyl) amide dihydrochloride, L-Ornithine-bis-(O,O'-myristoyl-β-hydroxyethyl)amide dihydrochloride, L-Ornithine-bis-(O,O'-oleoyl-β-hydroxyethyl)amide dihydrochloride, 1,4-bis [(3-(3-aminopropyl)-oleylamino)-2-hydroxypropyl] piperazine, L-Ornithine-bis-(O,O'-palmitoyl-β-hydroxyethyl)amide dihydrochloride, 1,4,-bis[(3-amino-2-hydroxypropyl)-oleylamino)-butane-2,3-diol, 1,4,-bis[(3-amino-2-hydroxypropyl)-palmitylamino]-butane-2,3-diol, 1,4,-bis[(3-amino-2-hydroxypropyl)-myristylamino]-butane-2,3-diol, 1,4-bis[(3-oleylamino)propyl]piperazine, L-Arginine-bis-(O,O'-oleoyl-β-hydroxyethyl)amide dihydrochloride, bis[(3-(3-aminopropyl)-myristylamino)2-hydroxypropyl]piperazine, L-Arginine-bis-(O,O'-palmitoyl-β-hydroxyethyl)amide dihydrochloride, L-Serine-bis-(O,O'-oleoyl-β-hydroxyethyl)amide dihydrochloride, 1,4-bis[(3-(3-aminopropyl)-palmitylamino)-2-hydroxypropyl] piperazine, Glycine-bis-(O,O'-palmitoyl-β-hydroxyethyl) amide dihydrochloride, Sarcosine-bis-(O,O'-palmitoyl-β-hydroxyethyl)amide dihydrochloride, L-Histidine-bis-(O,O'-palmitoyl-β-hydroxyethyl)amide dihydrochloride, cholesteryl-3β-carboxyl-amidoethylenetrimethylammonium iodide, 1,4-bis[(3-myristamino)propyl]piperazine, 1-dimethylamino-3-trimethylammonio-DL-2-propyl-cholesteryl carboxylate iodide, cholesteryl-3β-carboxyamidoethyleneamine, cholesteryl-3β-oxysuccinamidoethylenetrimethylammonium iodide, 1-dimethylamino-3-trimethylammonio-DL-2-propyl-cholesteryl-3β-oxysuccinate iodide, 2-[(2-trimethylammonio)-ethylmethylamino]ethyl-cholesteryl-3β-oxysuccinate iodide, 3β[N—(N',N'-dimethylaminoethane)carbamoyl] cholesterol, and 3β-[N-(polyethyleneimine)-carbamoyl] cholesterol, 1,4-bis[(3-palmitylamino)propyl]piperazine, L-ornithylglycyl-N-(1-heptadecyloctadecyl)glycinamide, $N^2,N^5$-Bis(3-aminopropyl)-L-ornithylglycyl-N-(1-heptadecyloctadecyl)glycinamide, 1,4-bis[(3-(3-amino-2-hydroxypropyl)-alkylamino)-2-hydroxypropyl]piperazine $N^2$—[$N^2,N^5$-Bis(3-aminopropyl)-L-ornithyl]-N,N-dioctadecyl-L-glutamine, $N^2$—[$N^2,N^5$-Bis(aminopropyl)-L-ornithyl]-N—N-dioctadecyl-L-α-glutamine, 1,4-bis[(3-(3-amino-2-hydroxypropyl)-oleylamino)2-hydroxypropyl] piperazine, $N^2$—[$N^2,N^5$-Bis(aminopropyl)-L-ornithyl]-N—N-dioctadecyl-L-α-asparagine, N—[$N^2$—[$N^2,N^5$-Bis[(1,1-dimethylethoxy)carbonyl]-$N^2,N^5$-bis[3-[(1,1-dimethylethoxy)carbonyl]aminopropyl]-L-ornithyl-N—N-dioctadecyl-L-glutaminyl]-L-glutamic acid, $N^2$—[$N^2,N^5$-Bis(3-aminopropyl)-L-ornithyl]-N,N-dioleyl-L-glutamine, $N^2$—[$N^2,N^5$-Bis(aminopropyl)-L-ornithyl]-N—N-dioleyl-L-α-glutamine, 4-bis[(3-(3-amino-2-hydoxypropyl)-myristylamino)-2-hydroxypropyl]piperazine, $N^2$—[$N^2,N^5$-Bis(aminopropyl)-L-ornithyl]-N—N-dioleyl-L-α-asparagine, N—[$N^2$—[$N^2,N^5$-Bis[(1,1-dimethylethoxy)carbonyl]-$N^2$,$N^5$-bis[3-[(1,1-dimethylethoxy)carbonyl]aminopropyl]-L-ornithyl-N—N-dioleyl-L-glutaminyl]-L-glutamic acid, 1,4-bis[(3-(3-aminopropyl)-oleylamino)propyl]piperazine, $N^2$—[$N^2,N^5$-Bis(3-aminopropyl)-L-ornithyl]-N,N-dipalmityl-L-glutamine, $N^2$[$N^2,N^5$-Bis(aminopropyl)-L-ornithyl]-N—N-dipalmityl-L-α-glutamine, $N^2$—[$N^2,N^5$-Bis(aminopropyl)-L-ornithyl]-N—N-dipalmityl-L-α-asparagine, N—[$N^2$—[$N^2,N^5$-Bis[(1,1-dimethylethoxy)carbonyl]-$N^2$,$N^5$-bis[3-[(1,1-dimethylethoxy)carbonyl]aminopropyl]-L-ornithyl-N—N-dipalmityl-L-glutaminyl]-L-glutamic acid, $N^2$—[$N^2,N^5$-Bis(3-aminopropyl)-L-ornithyl]-N,N-dimyristyl-L-glutamine, $N^2$—[$N^2,N^5$-Bis(aminopropyl)-L-ornithyl]-N—N-dimyristyl-L-α-glutamine, $N^2$—[$N^2,N^5$-Bis(aminopropyl)-L-ornithyl]-N—N-dimyristyl-L-α-asparagine, 1,4-bis[(3-(3-amino-2-hydroxypropyl)-palmitylamino)-2-hydroxypropyl]piperazine, N—[$N^2$—[$N^2,N^5$-Bis[(1,1-dimethylethoxy)carbonyl]-$N^2,N^5$-bis[3-[(1,1-dimethylethoxy)carbonyl]aminopropyl]-L-ornithyl-N—N-dimyristyl-L-glutaminyl]-L-glutamic acid, 1,4-bis [(3-(3-aminopropyl)-myristylamino)propyl]piperazine, $N^2$—[$N^2,N^5$-Bis(3-aminopropyl)-L-ornithyl]-N,N-dilaureyl-L-glutamine, $N^2$—[$N^2,N^5$-Bis(aminopropyl)-L-ornithyl]-N—N-dilaureyl-L-α-glutamine, $N^2$—[$N^2,N^5$-Bis(aminopropyl)-L-ornithyl]-N—N-dilaureyl-L-α-asparagine, N—[$N^2$—[$N^2,N^5$-Bis[(1,1-dimethylethoxy)carbonyl]-$N^2$,$N^5$-bis[3-[(1,1-dimethylethoxy)carbonyl]aminopropyl]-L-ornithyl-N—N-dilaureyl-L-glutaminyl]-L-glutamic acid, 3-[N',N"-bis(2-tertbutyloxycarbonylaminoethyl)guanidino]-N,N-dioctadec-9-enylpropionamide, 3-[N',N"-bis(2-tertbutyloxycarbonylaminoethyl)guanidino]-N,N-dipalmitylpropionamide, 3-[N',N"-bis(2-tertbutyloxycarbonylaminoethyl)guanidino]-N,N-dimyristylpropionamide, 1,4-bis[(3-(3-aminopropyl)-palmitylamino)propyl]piperazine, 1,4-bis[(3-(3-amino-2-hydroxypropyl)-oleylamino)propyl]piperazine, N,N-(2-hydroxy-3-aminopropyl)-N-2-hydroxypropyl-3-N,N-diolylaminopropane, N,N-(2-hydroxy-3-aminopropyl)-N-2-hydroxypropyl-3-N,N-dipalmitylaminopropane, N,N-(2-hydroxy-3-aminopropyl)-N-2-hydroxypropyl-3-N,N-dimyristylaminopropane, 1,4-bis[(3-(3-amino-2-hydoxypropyl)-myristylamino)propyl]piperazine, [(3-aminopropyl)-bis-(2-tetradecyloxyethyl)]methyl ammonium bromide, [(3-aminopropyl)-bis-(2-oleyloxyethyl)]methyl ammonium bromide, [(3-aminopropyl)-bis-(2-palmityloxyethyl)]methyl ammonium bromide, Oleoyl-2-hydroxy-3-N,N-dimethyamino propane, 2-didecanoyl-1-N,N-dimethylaminopropane, palmitoyl-2-hydroxy-3-N,N-dimethyamino propane, 1,2-dipalmitoyl-1-N,N-dimethylaminopropane, myristoyl-2-hydroxy-3-N,N-dimethyamino propane, 1,2-dimyristoyl-1-N,N-dimethylaminopropane, (3-Amino-propyl)→4-(3-aminopropylamino)-4-tetradecylcarbamoyl-butylcarbamic acid cholesteryl ester, (3-Amino-propyl)→4-(3-amino-propylamino-4-carbamoylbutylcarbamic acid cholesteryl ester, (3-Amino-propyl)→4-(3-amino-propylamino)-4-(2-dimethylamino-ethylcarbamoyl)-butylcarbamic acid cholesteryl ester, Spermine-5-carboxyglycine (N'-stearyl-N'-oleyl) amide tetratrifluoroacetic acid salt, Spermine-5-carboxyglycine (N'-stearyl-N'-elaidyl) amide tetratrifluoroacetic acid salt, Agmatinyl carboxycholesterol acetic acid salt, Spermine-5-carboxy-β-alanine cholesteryl ester tetratrifluoroacetic acid salt, 2,6-Diaminohexanoeyl β-alanine cholesteryl ester bistrifluoroacetic acid salt, 2,4-Diaminobutyroyl β-alanine cholesteryl ester bistrifluoroacetic acid salt, N,N-Bis(3-aminopropyl)-3-aminopropionyl β-alanine cholesteryl ester tristrifluoroacetic acid salt, [N,N-Bis(2-hydroxyethyl)-2-aminoethyl]aminocarboxy cholesteryl ester, Stearyl carnitine ester, Palmityl carnitine ester, Myristyl carnitine ester, Stearyl stearoyl carnitine ester chloride salt, L-Stearyl Stearoyl Carnitine Ester, Stearyl oleoyl carnitine ester chloride, Palmityl palmitoyl carnitine ester chloride, Myristyl myristoyl carnitine ester chloride, L-Myristyl myristoyl carnitine ester chloride, 1,4-bis[(3-(3-amino-2-hydroxypropyl)-palmitylamino)propyl]piperazine, N-(3-aminopropyl)-N,N-bis-(dodecyloxyethyl)-piperazinium bromide, N-(3-aminopropyl)-N,N-bis-(oleyloxyethyl)-piperazinium bromide, N-(3-aminopropyl)-N,N-bis-(palmityloxyethyl)-piperazinium bromide, N-(3-aminopropyl)-N,N-bis-(myristyloxyethyl)-piperazinium bromide, N-(3-aminopropyl)-N'-methyl-N,N'-(bis-2-dodecyloxyethyl)-piperazinium bromide, N-(3-aminopropyl)-N'-methyl-N,N'-(bis-2-oleyloxyethyl)-piperazinium bromide, N-(3-aminopropyl)-N'- methyl-N,N'-(bis-2-palmityloxyethyl)-piperazinium bromide, N-(3-aminopropyl)-N'-methyl-N,N'-(bis-2-myristyloxyethyl)-piperazinium bromide, 1,4-bis[(3-(3-aminopropyl)-oleylamino)-2-hydroxy-propyl]piperazine, 1,4-bis[(3-(3-aminopropyl)-myristylamino)-2-hydroxy-propyl]piperazine, or 1,4-bis[(3-(3-aminopropyl)-palmitylamino)-2-hydroxy-propyl]piperazine.

When the composition contains a neutral lipid, that lipid may be, for example, DOPE, DPhPE, cholesterol, DOPC, Lyso-PE (1-acyl-2-hydroxy-sn-glycero-3-phosphoethanolamine), Lyso-PC (1-acyl-3-hydroxy-sn-glycero-3-phosphocholine), or 3-alkyloxy-2-hydroxy-1-acetamidopropane. The composition may contain more than one of these neutral lipids.

Further provided are compositions containing a compound of structure (I) as described above and a polyamine transfection agent. The polyamine transfection agent may be, for example, selected from the group consisting of dense star dendrimers, PAMAM dendrimers, $NH_3$ core dendrimers, ethylenediamine core dendrimers, dendrimers of generation 5 or higher, dendrimers with substituted groups, dendrimers comprising one or more amino acids, grafted dendrimers, activated dendrimers, polyethylenimine, and polyethylenimine conjugates.

Also provided are compositions containing a compound of formula (I) as described above and a fusion agent. The fusion agent optionally may comprise a polycationic nucleic acid binding moiety. One or more cationic and/or neutral lipids may be present in these compositions.

Further provided are compositions containing a compound of formula (I) as described above and a cell surface ligand. The cell surface ligand optionally may comprise a polycationic nucleic acid binding moiety. These compositions may also contain one or more cationic and/or neutral lipids and/or a fusion agent.

In addition, compositions are provided containing a compound of formula (I) as described above and a nuclear localization peptide or protein cell surface ligand. These compositions may also contain one or more cationic and/or neutral lipids and/or a fusion agent and/or a cell surface ligand. The cell surface ligand and/or the nuclear localization peptide optionally may comprise a polycationic nucleic acid binding moiety.

The compositions may also contain an amphipathic peptide, which in some embodiments may also function as a fusion agent. Suitable amphipathic peptides include, but are not limited to, peptides comprising a sequence selected from the group consisting of FEAALAEALAEALA (SEQ ID No.: 10), Ac-LARLLPRLLARL-NHCH3 (SEQ ID No.: 11), GLLEELLELLEELWEELLEG (SEQ ID No.: 12), GWEGLIEGIEGGWEGLIEG(SEQ ID No.: 13), GLFEALAEFIEGGWEGLIEG (SEQ ID No.: 14), GLFEALLELLESLWELLLEA (SEQ ID No.: 15), GGYCLEKWMIVASELKCFGNTA (SEQ ID No.: 16), GGYCLTRWMLIEAELKCFGNTAV (SEQ ID No.: 17), and WEAALAEALAEALAEHLAEALAEALEALAA (SEQ ID No.: 18). The amphipathic peptide may optionally be linked to a polycationic nucleic acid binding moiety, for example via a covalent linkage.

Also provided are compositions as described above further comprising a nucleic acid. The nucleic acid may be, for example, an RNA molecule, such as an RNAi molecule.

Methods are provided of introducing a nucleic acid into a eukaryotic cell, comprising contacting the cell with a composition as described above, thereby introducing the nucleic acid. The cell may be an animal cell, for example a human cell.

Also provided are kits containing a compound of formula (I) and: a neutral lipid, a cationic lipid, a cell surface ligand, a fusion agent and/or a nuclear localization peptide or protein.

Further provided are methods of expressing a protein in a cell, comprising contacting the cell with an expression vector encoding the protein and a compound of formula (I) as described above or a composition as described above.

Methods are provided for inhibiting expression of a protein in a cell, in which the cell is contacted with an RNAi molecule and a compound according to claim 1.

In other embodiments of compounds of structure (I), $R^2$ may be $—CH_2—CHOH—(CHR^3)_{1-6}—NHR^4$, and advantageously may be $CH_2—CHOH—CH_2—NH_2$.

A specific example of a compound of structure (I) is

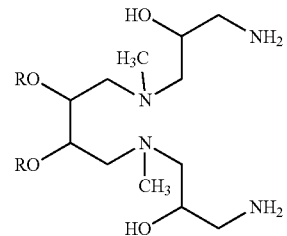

where R advantageously is $C_{12-20}$ alkyl or monounsaturated alkenyl.

In some embodiments at least two neutral lipids are present, which may, for example, be selected from the group consisting of DOPE, DPhPE, cholesterol, DOPC, Lyso-PE (1-acyl-2-hydroxy-sn-glycero-3-phosphoethanolamine), Lyso-PC (1-acyl-3-hydroxy-sn-glycero-3-phosphocholine), and 3-alkyloxy-2-hydroxy-1-acetamidopropane.

These compositions also may contain one or more polyamine transfection agent, such as dense star dendrimers, PAMAM dendrimers, $NH_3$ core dendrimers, ethylenediamine core dendrimers, dendrimers of generation 5 or higher, dendrimers with substituted groups, dendrimers comprising one or more amino acids, grafted dendrimers, activated dendrimers, polyethylenimine, and/or polyethylenimine conjugates.

The compositions may contain a fusion agent, a cell surface ligand. a nuclear localization peptide or protein, amphipathic peptide and/or a nuclear localization agent. A nucleic acid also may be present. The fusion agent, cell surface ligand, nuclear localization peptide and/or amphipathic peptide optionally may comprise a polycationic nucleic acid binding moiety.

Also provided are methods of introducing a nucleic acid into a eukaryotic cell, comprising contacting the cell with a composition as described above, thereby introducing the nucleic acid, into the cell, for example a human cell or an animal cell. The nucleic acid may, for example, be an expression vector.

Also provided are methods of inhibiting expression of a protein in a cell, comprising contacting the cell with a double stranded RNAi molecule and a compound according to formula (I), or a composition containing that compound.

Also provided are methods of expressing a protein in a cell, comprising contacting the cell with an expression vector encoding the protein and a compound of formula (I), or a composition containing that compound.

Also provided is a method of increasing the transfection efficiency of a polycationic lipid containing N amine groups, comprising contacting said cationic lipid with an acylating reagent in an amount sufficient to acylate no more than N−1 of the amine groups.

Also provided are compositions comprising an amphipathic peptide optionally comprising a polycationic nucleic acid binding moiety and a compound having the structure (II):

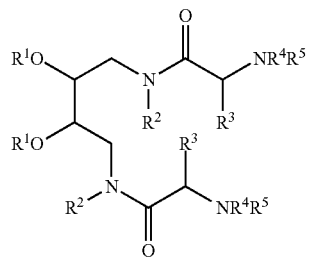

where each $R^1$ independently is $C_1$-$C_{23}$ alkyl, $C_1$-$C_{23}$ alkenyl, —(CO)$C_1$-$C_{23}$ alkyl, or —(CO)$C_1$-$C_{23}$ alkenyl; each $R^2$ independently is $C_1$-$C_6$ alkyl, or $C_1$-$C_6$ alkenyl, optionally interrupted by O; each $R^3$ independently is H, $C_1$-$C_6$ alkyl, $C_1$-$C_6$ alkenyl, $C_2$-$C_6$ alkynyl, $C_3$-$C_7$ cycloalkyl, $C_3$-$C_7$ cycloalkyl-$C_1$-$C_6$ alkyl, $C_5$-$C_7$-cycloalkenyl, $C_5$-$C_7$-cycloalkenyl-$C_1$-$C_6$ alkyl, —(CH$_2$)$_m$NR$^6$(CH$_2$)$_n$NHR$^7$, —(CH$_2$)$_{2-6}$NHR$^7$, —(CH$_2$)$_{3-6}$NHC(=NH)NH$_2$, ((CH$_2$)$_m$O$_x$)$_y$(CH$_2$)$_z$O$_x$R$^8$, or —(CH$_2$)$_{0-3}$Het; each $R^4$ independently is H, $C_1$-$C_6$ alkyl, or $C_1$-$C_6$ alkenyl; each $R^5$ independently is H, an amine protecting group, —(CH$_2$)$_m$NR$^6$(CH$_2$)$_n$NHR$^7$, —(CH$_2$)$_{2-6}$NHR$^7$, —(CH$_2$)$_{3-6}$NHC(=NH)NH$_2$, —(CO)$C_1$-$C_{23}$ alkyl, —(CO)$C_1$-$C_{23}$ alkenyl, or a peptide containing 1-20 amino acid residues; each m independently is 2-5, each n independently is 2-5, each x independently is 0 or 1, y is 0-2, z is 1-6, $R^6$ and $R^7$ independently are H, an amine protecting group, —(CO)$C_1$-$C_{23}$ alkyl, or —(CO)$C_1$-$C_{23}$ alkenyl; $R^8$ is H, $C_1$-$C_6$ alkyl, or $C_1$-$C_6$ alkenyl, and Het is a 5-7 membered monocyclic basic heterocycle, or an 8-11 membered bicyclic basic heterocycle. These compositions also may include one or more reagents such as a cationic lipid, a cell surface ligand, a cell surface ligand comprising a polycationic nucleic acid binding moiety, a fusion agent, a fusion agent comprising a polycationic nucleic acid binding moiety, a nuclear localization peptide or protein, and a nuclear localization peptide or protein comprising a polycationic nucleic acid binding moiety. Advantageously, these compositions contain a compound of structure (II), an amphipathic peptide optionally comprising a polycationic nucleic acid binding moiety, a cationic lipid and a cell surface ligand comprising a polycationic nucleic acid binding moiety.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 1(A) and 1(B) show the results of transfection of a β-galactosidase gene into 293 GT and CHO K1 cells respectively, compared to the results obtained using commercial reagents.

FIGS. 2(A) and 2(B) show the results of transfection of a β-galactosidase gene into HeLa and NIH 3T3 cells respectively, compared to the results obtained using commercial reagents.

FIGS. 3(A) and 3(B) show the results of transfection of a β-galactosidase gene into A549 and HMSC-Ad cells respectively, compared to the results obtained using commercial reagents.

FIGS. 4(A) and 4(B) show the results of transfection of a β-galactosidase gene into Nuff and UB Stem cells respectively, compared to the results obtained using commercial reagents.

DETAILED DESCRIPTION

Positively charged (cationic) molecules are provided that are useful for improved methods of delivering macromolecules into eukaryotic cells. The compositions and methods are effective in a wide variety of cells, and provide a high efficiency of transfection. Specifically, it has been found that molecules based on a core of N,N'-disubstituted 2,3,-dihydroxy-1,4-butanediamine are useful for efficient delivery of macromolecules into cells. These molecules advantageously can be used with one or more neutral lipids and additional components such as fusogenic or fusion-enhancing molecules, additional cationic lipids, cell surface ligands, cell adhesion molecules, and nuclear localization agents, in a complex with the macromolecule. The complex is easily prepared by straightforward methods and can be used on a wide variety of cells.

Surprisingly, it also has been found that the nucleic acid transfection efficiency of cationic lipids in general, and the new cationic lipids described herein in particular, can be dramatically enhanced in many cases by reducing the net positive charge on the lipid by partial acylation of free primary and secondary amine functions on the lipid. Unexpectedly, this reduction in charge has been shown to greatly increase the ability of transfection complexes containing the modified lipid to efficiently transfect cells. Thus, for a lipid with N primary or secondary amines, it is possible to acylate up to N−1 of the amine groups. In most cases, the skilled artisan will recognize that the distribution of acyl groups in a lipid preparation with distinct amino groups will be statistical, because regiospecific acylation likely will not be possible unless the acylation is carried out as part of a more elaborate synthetic scheme. Thus the distribution of acyl groups will be affected not only by the stoichiometry of the acylation reagent with respect to the lipid, but will also be affected by the reactivity of the amine groups, both initially (in the non-acylated amine) but also during the reaction, as acylation activity at a free amine is potentially affected by acylation at another amine elsewhere in the molecule.

The enhancement of transfection is particularly marked for lipids containing 4 or more reactive amines, in addition to the possible presence of tertiary or quaternary amines, but is not necessarily limited to these lipids. This observed result is surprising in light of the prejudice in the art that a relatively high charge on a cationic lipid is desirable to enhance binding of negatively charged nucleic acids.

New Cationic Lipids
New lipid molecules are provided having the structure (I):

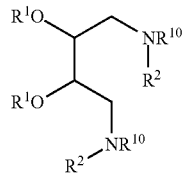

where each $R^1$ independently is $C_1$-$C_{23}$ alkyl, $C_1$-$C_{23}$ alkenyl, —(CO)$C_1$-$C_{23}$ alkyl, or —(CO)$C_1$-$C_{23}$ alkenyl; and each $R^2$ independently is —CH$_2$—(CHR$^3$)$_{1-6}$—CH$_2$—NHR$^4$ or CH$_2$—(CHR$^3$)$_{0-6}$—CH$_2$—OH, where each $R^3$ independently is H, OH, or NH$_2$, $R^4$ is H or CH$_3$; and $R^{10}$ is H or $C_1$-$C_8$ alkyl.

In one embodiment, $R^1$ may be $C_{14}$-$C_{20}$ alkyl or monounsaturated $C_{14}$-$C_{20}$-alkenyl. In this and other embodiments, $R^2$ may be —CH$_2$—(CHR$^3$)$_{1-6}$—CH$_2$—NHR$^4$ and $R^3$ is H or OH. In some embodiments, no more than 3 $R^3$ groups are OH in each $R^3$ moiety.

In any of these embodiments, each $R^1$ may be the same or different, and each $R^2$ may be the same or different. In specific embodiments, one or both $R^{10}$ may be H, or one or both $R^{10}$ may be $C_1$-$C_3$ alkyl, for example, one or both $R^{10}$ may be methyl.

In particular embodiment above, one or both $R^1$ may be $C_{12}$-$C_{20}$ alkenyl, and the alkenyl moieties may be cis alkenyl.

In specific embodiments, one or both $R^2$ may be —CH$_2$—CHOH—(CHR$^3$)$_{0-5}$—CH$_2$—NHR$^4$; for example one or both $R^2$ may be —CH$_2$—CHOH—CH$_2$—NH$_2$. In these compounds R advantageously is $C_{14-18}$ alkyl or $C_{14-18}$ monounsaturated alkenyl.

Each $R^1$, $R^2$ and/or each $R^{10}$ may be the same or different and thus the molecule may be symmetrical or non-symmetrical. In particular embodiments, $R^2$ may be $C_1$-$C_3$ alkyl and/or $R^1$ is monounsaturated $C_{12}$-$C_{20}$ alkenyl. One or both $C_{12}$-$C_{20}$ alkenyl moieties in $R^1$, when present, may be cis alkenyl.

Also provided are molecules having the structure (II)

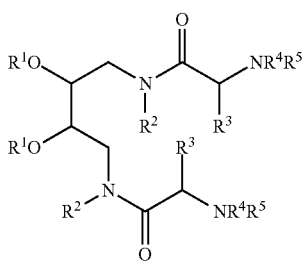

In this structure, each $R^1$ independently may be $C_1$-$C_{23}$ alkyl, $C_1$-$C_{23}$ alkenyl, —(CO)$C_1$-$C_{23}$ alkyl, or —(CO)$C_1$-$C_{23}$ alkenyl. Each $R^2$ independently may be $C_1$-$C_6$ alkyl, or $C_1$-$C_6$ alkenyl, optionally interrupted by up to 2 O atoms. Each $R^3$ independently may be H, $C_1$-$C_6$ alkyl, $C_1$-$C_6$ alkenyl, $C_2$-$C_6$ alkynyl, $C_3$-$C_7$ cycloalkyl, $C_3$-$C_7$ cycloalkyl-$C_1$-$C_6$ alkyl, $C_5$-$C_7$-cycloalkenyl, $C_5$-$C_7$-cycloalkenyl-$C_1$-$C_6$ alkyl, —(CH$_2$)$_m$NR$^6$(CH$_2$)$_n$NHR$^7$, —(CH$_2$)$_{2-6}$NHR$^7$, —(CH$_2$)$_{3-6}$NHC(=NH)NH$_2$, ((CH$_2$)$_m$O$_x$)$_y$(CH$_2$)$_z$O$_x$R$^8$, or —(CH$_2$)$_{0-3}$Het. Each $R^4$ independently may be H, $C_1$-$C_6$ alkyl, or $C_1$-$C_6$ alkenyl and each $R^5$ independently may be H, an amine protecting group, —(CH$_2$)$_m$NR$^6$(CH$_2$)$_n$NHR$^7$, —(CH$_2$)$_{2-6}$NHR$^7$, —(CH$_2$)$_{3-6}$NHC(=NH)NH$_2$, —(CO)$C_1$-$C_{23}$ alkyl, —(CO)$C_1$-$C_{23}$ alkenyl, or a peptide containing 1-20 amino acid residues. The peptide advantageously contains multiple positively charged amino acid side chains. Thus, for example, the peptide may contain one or more lysine, arginine, and/or histidine residues. Other positively charged amino acids also may be used, whether or not naturally occurring. Thus, for example, ornithine, homoarginine and other amino acids containing amine, guanidine; imidazole and other basic heterocycles and the like can be used. Each m independently may be 2-5, and each n independently may be 2-5, while each x independently may be 0 or 1, each y may be 0-2, and each z may be 1-6. $R^6$ and $R^7$ independently may be H, an amine protecting group, —(CO)$C_1$-$C_{23}$ alkyl, or —(CO)$C_1$-$C_{23}$ alkenyl, $R^8$ may be H, $C_1$-$C_6$ alkyl, or $C_1$-$C_6$ alkenyl, and Het may be a 5-7 membered monocyclic basic heterocycle, or an 8-11 membered bicyclic basic heterocycle.

The molecule of structure (II) may be symmetrical or non-symmetrical with regard to each or all of the substituents $R^1$-$R^5$ independently; that is each $R^1$ may be the same or different, each $R^2$ may be the same or different, each $R^3$ may be the same or different, each $R^4$ may be the same or different, and/or each $R^5$ may be the same or different.

In specific embodiments of structure (II) $R^2$ may be $C_1$-$C_3$ alkyl and/or $R^1$ may be monounsaturated $C_{12}$-$C_{20}$ alkenyl; for example one or both $C_{12}$-$C_{20}$ alkenyl moieties in $R^1$ may be cis alkenyl.

In other embodiments of structure (II), $R^3$ may be —(CH$_2$)$_m$NR$^6$(CH$_2$)$_n$NHR$^7$ and/or $R^5$ may be —(CH$_2$)$_{2-6}$NHR$^7$. In these or other embodiments, m may be 3, n may be 3, and/or $R^5$ may be —(CH$_2$)$_3$NHR$^7$ In these and other embodiments, each $R^6$ and each $R^7$ may be H.

In still other embodiments of structure (II), at least one $R^6$ or $R^7$ may be —(CO)$C_1$-$C_{23}$ alkyl, or —(CO)$C_1$-$C_{23}$ alkenyl and the remainder are H. In a specific embodiment, each $R^1$ may be $C_{12}$-$C_{20}$ alkyl or $C_{12}$-$C_{20}$ monounsaturated alkenyl, each $R^2$ may be $C_1$-$C_3$ alkyl, each $R^3$ may be —(CH$_2$)$_3$NH(CH$_2$)$_3$NH$_2$, each $R^4$ may be H; and each $R^5$ may be —(CH$_2$)$_3$NH$_2$. In another specific embodiment, each $R^1$ may be $C_{12}$-$C_{20}$ alkyl or $C_{12}$-$C_{20}$ monounsaturated alkenyl, each $R^2$ may be $C_1$-$C_3$ alkyl, each $R^3$ may be —(CH$_2$)$_3$NR$^6$(CH$_2$)$_3$NHR$^7$, each $R^4$ may be H; each $R^5$ may be —(CH$_2$)$_3$NHR7, and at least one $R^6$ or $R^7$ may be —(CO)$C_1$-$C_{23}$ alkyl, or —(CO)$C_1$-$C_{23}$ alkenyl and the remainder are H.

Specific examples of compounds of structure (II) include compounds having the structure:

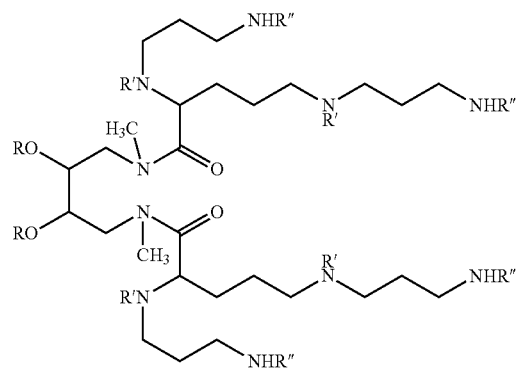

where each R for example may be, but is not limited to, $C_{12-20}$ alkyl or $C_{12-20}$ alkenyl; and each R' and each R" independently may be, but is not limited to, H, an amine protecting group, —(CO)$C_1$-$C_{23}$ alkyl, or —(CO)$C_1$-$C_{23}$ alkenyl.

In these and other embodiments of structure (II), R may be $C_{14}$-$C_{18}$ alkyl or $C_{14}$-$C_{18}$ alkenyl, and/or each R' and each R" independently may be H, $C_{14}$-$C_{18}$ alkyl or $C_{14}$-$C_{18}$ alkenyl.

Another specific example of the compounds of structure (II) is the set of compounds having the structure:

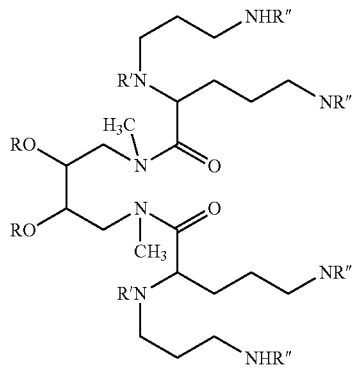

where, for example, R may be, but is not limited to, $C_{12-20}$ alkenyl; and/or each R' and each R" independently may be, but is not limited to, H, an amine protecting group, —(CO)$C_1$-$C_{23}$ alkyl, or —(CO)$C_1$-$C_{23}$ alkenyl.

In these and other embodiments R may be oleyl and each R' and each R" independently may be H, or oleoyl. In still other embodiments at least one R' or R" may be oleoyl and the remainder are H.

In still other specific embodiments of structure (II), each $R^3$ independently may be —$(CH_2)_{2-6}NHR^7$, —$(CH_2)_{3-6}NHC(=NH)NH_2$, or —$(CH_2)_{1-3}$Het, each $R^4$ is H and each $R^5$ independently is H or a peptide containing 1-20 amino acid residues.

In these and other embodiments, each $R^1$ may be $C_{12}$-$C_{20}$ alkyl or $C_{12}$-$C_{20}$ alkenyl, each $R^2$ may be $C_1$-$C_3$ alkyl, and/or and each $R^5$ may be H. In still other embodiments, each $R^3$ may be —$(CH_2)_{2-6}NH_2$, —$(CH_2)_{3-6}NHC(=NH)NH_2$ or each $R^3$ may be —$(CH_2)_{1-3}$Het. In one specific embodiment, Het may be

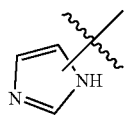

The skilled artisan will recognize that, although the molecules of the invention are shown here for convenience in their neutral (unprotonated) forms, these molecules will exist in a partially or fully protonated form in solutions of appropriate pH, and that the present invention encompasses the molecules in all their protonated, unprotonated, ionized and non-ionized forms without limitation, unless specifically indicated otherwise.

Definitions

The term "alkyl", alone or in combination with any other term, refers to a straight-chain or branch-chain saturated aliphatic hydrocarbon radical containing the specified number of carbon atoms, or where no number is specified, in one embodiment from 1 to about 15 (i.e. ($C_{1-15}$)alkyl), in another embodiment from 1 to about 10 carbon atoms (i.e. ($C_{1-10}$) alkyl), and in another embodiment from 1 to about 6 carbon atoms (i.e. ($C_{1-6}$)alkyl). Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl", alone or in combination with any other term, refers to a straight-chain or branched-chain mono- or poly-unsaturated aliphatic hydrocarbon radical containing the specified number of carbon atoms, or where no number is specified, in one embodiment from 2-10 carbon atoms (i.e. ($C_{2-10}$)alkenyl) and in another embodiment, from 2-6 carbon atoms (i.e. ($C_{2-6}$)alkenyl). Examples of alkenyl radicals include, but are not limited to, ethenyl, E- and Z-propenyl, isopropenyl, E- and Z-butenyl, E- and Z-isobutenyl, E- and Z-pentenyl, E- and Z-hexenyl, E,E-, E,Z-, Z,E- and Z,Z-hexadienyl and the like.

The term "alkynyl," alone or in combination with any other term, refers to a straight-chain or branched-chain hydrocarbon radical having one or more triple bonds containing the specified number of carbon atoms, or where no number is specified, in one embodiment from 2 to about 10 carbon atoms. Examples of alkynyl radicals include, but are not limited to, ethynyl, propynyl, propargyl, butynyl, pentynyl and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "aryl," alone or in combination with any other term, refers to a carbocyclic aromatic radical (such as phenyl or naphthyl) containing the specified number of carbon atoms, in one embodiment from 6-15 carbon atoms (i.e. ($C_{6-15}$)aryl), and in another embodiment from 6-10 carbon atoms (i.e. ($C_{6-10}$)aryl), optionally substituted with one or more substituents selected from alkyl, alkoxy, (for example methoxy), nitro, halogen, (for example chloro), amino, carboxylate and hydroxy. Examples of aryl radicals include, but are not limited to phenyl, p-tolyl, 4-hydroxyphenyl, 1-naphthyl, 2-naphthyl, indenyl, indanyl, azulenyl, fluorenyl, anthracenyl and the like.

The term "aralkyl", alone or in combination, means an alkyl radical as defined above in which one hydrogen atom is phenyl, benzyl, 2-phenylethyl and the like.

The term "aralkoxycarbonyl", alone or in combination, means a radical of the formula —C(O)—O-aralkyl in which the term "aralkyl" has the significance given above. An example of an aralkoxycarbonyl radical is benzyloxycarbonyl.

The term "aryloxy", alone or in combination, means a radical of the formula aryl-O— in which the term "aryl" has the significance given above.

The term "alkanoyl", alone or in combination, means an acyl radical derived from an alkanecarboxylic acid, examples of which include acetyl, propionyl, butyryl, valeryl, 4-methylvaleryl, and the like.

The term "aryloxyalkanoyl" means an acyl radical of the formula aryl-O-alkanoyl wherein aryl and alkanoyl have the significance given above.

The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-phenylbutyryl, (1-naphthyl)acetyl, 4-chlorohydrocinnamoyl, 4-aminohydrocinnamoyl, 4-methoxyhydrocinnamoyl, and the like.

The term "aroyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "aminocarbonyl" alone or in combination, means an amino-substituted carbonyl (carbamoyl) group derived from an amino-substituted carboxylic acid wherein the amino group can be a primary, secondary or tertiary amino group continuing substituents selected from hydrogen, alkyl, aryl, aralkyl, cycloalkyl, cycloalkylalkyl radicals and the like.

The term "aminoalkanoyl" means an acyl radical derived from an amino substituted alkanecarboxylic acid wherein the amino group can be a primary, secondary or tertiary amino group containing substituents selected from the group consisting of hydrogen, cycloalkyl, cycloalkylalkyl radicals and the like, examples of which include N,N-dimethylaminoacetyl and N-benzylaminoacetyl.

The term "carbocycle" refers to a non-aromatic stable 3- to 8-membered carbon ring which may be saturated, mono-unsaturated or poly-unsaturated. The carbocycle may be attached at any endocyclic carbon atom which results in a stable structure. Carbocycles in one embodiment have 5-7 carbons.

The term "cycloalkyl", alone or in combination, means an alkyl radical which contains from about 3 to about 8 carbon atoms and is cyclic. Examples of such cycloalkyl radicals include cyclopropyl, cyclobutyl, cyclopentyl, cyclohexyl and the like.

The term "cycloalkylalkyl" means an alkyl radical as defined above which is substituted by a cycloalkyl radical containing from about 3 to about 8, in one embodiment from about 3 to about 6, carbon atoms.

The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkanoylamino, such as 1,2,3,4-tetrahydro-2-naphthoyl, 2-acetamido-1,2,3,4-tetrahydro-2-naphthoyl.

The term "cycloalkylalkoxycarbonyl" means an acyl group derived from a cycloalkylalkoxycarboxylic acid of the formula cycloalkylalkyl-O—COOH wherein cycloalkylalkyl has the significance given above.

The term "basic heterocycle" refers to a stable 5-7 membered monocyclic heterocyclic ring or 8-11 membered bicyclic heterocyclic ring which is either saturated or partially unsaturated, and which may be optionally benzofused if monocyclic and which is optionally substituted on one or more carbon atoms by halogen, alkyl, alkoxy, oxo, and the like, and/or on a secondary nitrogen atom (i.e., —NH—) by alkyl, aralkoxycarbonyl, alkanoyl, phenyl or phenylalkyl or on a tertiary nitrogen atom (i.e., +N—) by oxido and which is attached via a carbon atom. Each heterocycle consists of one or more carbon atoms and from one to four heteroatoms selected from the group consisting of nitrogen, oxygen and sulfur, provided that at least one heteroatom is a basic nitrogen atom. A heterocyclyl radical may be attached at any endocyclic carbon or heteroatom which results in the creation of a stable structure. Heterocycles include 5-7 membered monocyclic heterocycles and 8-10 membered bicyclic heterocycles. Examples of basic heterocycles include imidazolinoyl, imidazolidinyl, indazolinolyl, perhydropyridazyl, pyrrolinyl, pyrrolidinyl, piperidinyl, pyrazolinyl, piperazinyl, morpholinyl, thiamorpholinyl, thiazolidinyl, thiamorpholinyl sulfone, oxopiperidinyl, oxopyrrolidinyl, and oxoazepinyl.

The term "halogen" means fluorine, chlorine, bromine or iodine.

The term "surface ligand" or "cell surface ligand" refers to a chemical compound or structure which will bind to a surface receptor of a cell. The term "cell surface receptor" as used herein refers to a specific chemical grouping on the surface of a cell to which the ligand can attach. Cell surface receptors can be specific for a particular cell, i.e., found predominantly in one cell rather than in another type of cell (e.g., LDL and asialoglycoprotein receptors are specific for hepatocytes). The receptor facilitates the internalization of the ligand and attached molecules. A cell surface receptor includes but is not limited to a folate receptor, biotin receptor, lipoic acid receptor, low-density lipoprotein receptor, asialoglycoprotein receptor, insulin-like growth factor type II/cation-independent mannose-6-phosphate receptor, calcitonin gene-related peptide receptor, insulin-like growth factor I receptor, nicotinic acetylcholine receptor, hepatocyte growth factor receptor, endothelin receptor, bile acid receptor, bone morphogenetic protein receptor, cartilage induction factor receptor or glycosylphosphatidylinositol (GPI)-anchored proteins (e.g., .beta. adrenergic receptor, T-cell activating protein, Thy-1 protein, GPI-anchored 5' nucleotidase). These are nonlimiting examples.

A receptor is a molecule to which a ligand binds specifically and with relatively high affinity. It is usually a protein or a glycoprotein, but may also be a glycolipid, a lipidpolysaccharide, a glycosaminoglycan or a glycocalyx. For purposes of this disclosure, epitopes to which an antibody or its fragments binds is construed as a receptor since the antigen: antibody complex undergoes endocytosis. Furthermore, surface ligand includes anything which is capable of entering the cell through cytosis (e.g. endocytosis, potocytosis, pinocytosis).

As used herein, the term "ligand" refers to a chemical compound or structure which will bind to a receptor. This includes but is not limited to ligands such as asialoorosomucoid, asialoglycoprotein, lipoic acid, biotin, apolipoprotein E sequence, insulin-like growth factor II, calcitonin gene-related peptide, thymopoietin, hepatocyte growth factor, endothelin-1, atrial natriuretic factor, RGD-containing cell adhesion peptides and the like.

One skilled in the art will readily recognize that the ligand chosen will depend on which receptor is being bound. Since different types of cells have different receptors, this provides a method of targeting nucleic acid to specific cell types, depending on which cell surface ligand is used. Thus, the preferred cell surface ligand may depend on the targeted cell type.

The term "nuclear localization agent," "nuclear localization signal," or "nuclear ligand" as used herein refers to a ligand, such as a peptide, which will cause an agent covalently or non-covalently linked to it to localize at the cell nucleus, typically by binding a nuclear receptor. The term "nuclear receptor" as used herein refers to a chemical grouping on the nuclear membrane which will bind a specific ligand and help transport the ligand, and accompanying linked moieties, through the nuclear membrane.

Nuclear receptors can be but are not limited to those receptors which bind nuclear localization sequences. Non-limiting examples of nuclear ligands include GYSTPPKKKRKVEDP (SEQ ID No.: 1), GYSTPPKTRRRP (SEQ ID No.: 2), GYSTPGRKKR (SEQ ID No.: 3), GYSTPRRNRRRRW (SEQ ID No.: 4), PDEVKRKKKPPTSYG (SEQ ID No.: 5), PRRRTKPPT-SYG (SEQ ID No.: 6), RKKRGPTSYG (SEQ ID No.: 7), WRRRRNRRPTSYG (SEQ ID No.: 8), and GYGPPKKKRKVEAPYKA(K)20-40K (SEQ ID No.: 9), may be used to transport nucleic acid to the nucleus.

The term "polycationic nucleic acid binding moiety" as used herein refers to a moiety containing multiple positive charges at physiological pH that allow the moiety to bind a negatively charged nucleic acid. A polycationic nucleic acid binding moiety may be linked to, for example, a cell surface ligand, a fusion agent, and/or a nuclear localization peptide. The linkage may be covalent. Suitable polycationic nucleic acid binding moieties include polyamines and polybasic peptides containing, for example, multiple lysine, ornithine, or histidine residues.

The term "lysis agent" as used herein refers to a molecule, compound, protein or peptide which is capable of breaking down an endosomal membrane and freeing the DNA transporter into the cytoplasm of the cell. This term includes but is not limited to viruses, synthetic compounds, lytic peptides, or derivatives thereof. The term "lytic peptide" refers to a chemical grouping which penetrates a membrane such that the structural organization and integrity of the membrane is lost. As a result of the presence of the lysis agent, the membrane undergoes lysis, fusion or both.

The term "nucleic acid," when not applied to a specific type of molecule such as unmodified DNA or RNA, refers to any type of nucleic acid that presently is known or that may be prepared or identified in the future, provided that the nucleic acid is sufficiently negatively charged to form a lipid aggregate, liposome, or liposome-like complex when admixed with any lipid of Formula (I) or (II). Nucleic acid, as used herein, refers to deoxyribonucleotides or ribonucleotides and mixtures and polymers thereof in single- or double-stranded form. The term encompasses nucleic acids containing known nucleotide analogs or modified backbone residues or linkages, which are synthetic, naturally occurring, and non-naturally occurring, which have similar binding properties as a reference nucleic acid, and which are metabolized in a manner similar to reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). The nucleic acid may be in the form of an antisense molecule, for example a "gap-mer" containing an RNA-DNA-RNA structure that activates RNAseH. The nucleic acid can be, for example, DNA or RNA, or RNA-DNA hybrid, and can be an oligonucleotide, plasmid, parts of a plasmid DNA, pre-condensed DNA, product of a polymerase chain reaction (PCR), vectors, expression cassettes, chimeric sequences, chromosomal DNA, or derivatives of these groups or other form of nucleic acid molecule. The nucleic acid may be a double-stranded RNA molecule of the type used for inhibiting gene expression by RNA interference. The nucleic acid may be a short interfering double stranded RNA molecule (siRNA). The nucleic acid molecule can also be a Stealth™ RNAi molecule (Invitrogen Corporation/Life Technologies Corporation, Carlsbad, Calif.).

The term "amphipathic peptide" refers to a peptide whose secondary structure places hydrophobic and hydrophilic amino acid residues on different faces of the peptide. The peptides often adopt a helical secondary structure. In some circumstances an amphipathic 15 peptide may also function as a fusion agent. Examples of amphipathic peptides suitable for use in the compositions described herein include, but are not limited to, peptides comprising a sequence selected from the group consisting of FEAALAEALAEALA (SEQ ID No.: 10), Ac-LARLLPRLLARL-NHCH3 (SEQ ID No.: 11), GLLEELLELLEELWEELLEG (SEQ ID No.: 12), GWEG-LIEGIEGGWEGLIEG(SEQ ID No.: 13), GLFEA-LAEFIEGGWEGLIEG (SEQ ID No.: 14), GLFEAL-LELLESLWELLLEA (SEQ ID No.: 15), GGYCLEKWMIVASELKCFGNTA (SEQ ID No.: 16), GGYCLTRWMLIEAELKCFGNTAV (SEQ ID No.: 17), and WEAALAEALAEALAEHLAEALAEALEALAA (SEQ ID No.: 18). The amphipathic peptide may optionally be linked to a polycationic nucleic acid binding moiety, for example via a covalent linkage.

Preparation of the Lipids

Symmetric and asymmetric cationic lipids of general structure (I) and (II) may be synthesized using methods that are well known in the art, as shown, for example in Scheme 1. Dimethyl tartrate (1) can be treated with an alkylamine at elevated temperature (e.g. 70° C.) in a sealed pressure reactor to obtain compound 2. This compound may be alkylated with an alkyl mesylate to obtain compound 3, which is then reduced using lithium aluminum hydride to produce the bis-amine 4. Compound 4 may be acylated with a suitably protected amino acid 5 using, for example, a carbodiimide as a coupling agent to obtain the protected precursor of compound 6. This precursor is then deprotected to produce the desired symmetric compound 6. Specific examples of suitable amino acids for the acylation include Boc-protected carboxyspermine, histidine or lysine, which generate compounds 7, 8, and 9 respectively, after deprotection.

Alternatively, asymmetric cationic lipids (i.e. compounds lacking a plane of symmetry) may be prepared using a tartaric acid monoester, readily prepared from diacetyl tartaric anhydride (see *Organic Syntheses, Coll. Vol.* 4, p. 242 (1963); *Vol.* 35, p. 49 (1955)) or from an erythronolactone such as 10. See Scheme 2. Protection of the diol, followed by DIBAL reduction, reductive amination and amine protection produce compound 11. Mild oxidation, reductive amination and protection produce compound 12. Diol deprotection and alkylation produce compound 13. Stepwise selective amine deprotection and coupling reactions then produces the asymmetric compound 14.

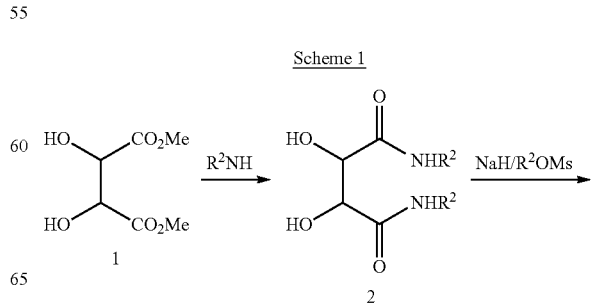

Scheme 1

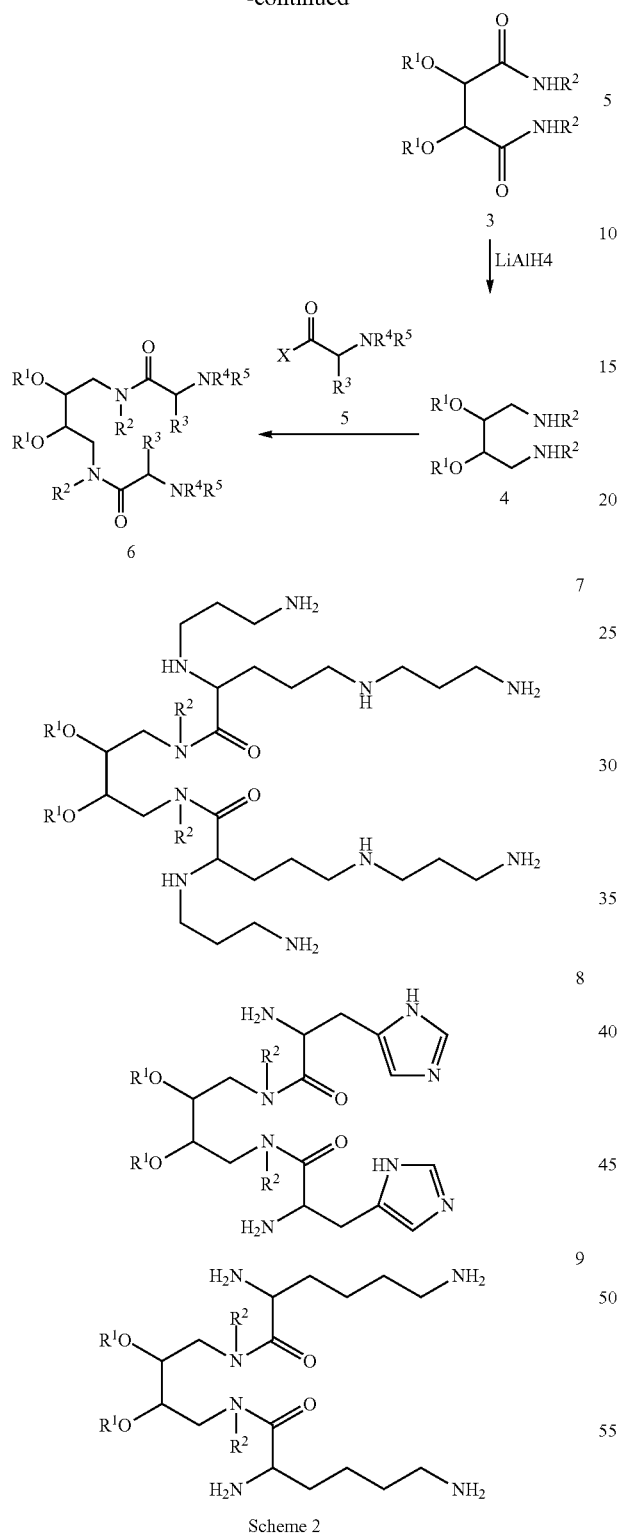

In an alternative synthesis, a bis-epoxide is reacted with an alkylamine to produce the amino alcohol 15. This can be acylated to produce 16 followed by alkylation and deprotection, if necessary, to produce 6. See Scheme 3.

Compounds of formula (I) may be prepared from intermediates of structure 4 above by methods that are well known in the art. For example, compound 4 where $R^2$ is alkyl may be reacted with a suitable protected epoxyamine, for example, an epoxyphthalimide, followed by deprotection to provide β-hydroxyamines such as

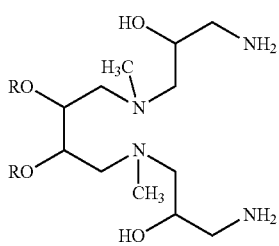

Other methods of preparing compounds of formula (II) will be apparent to the skilled artisan. For example, reductive amination of a protected carbohydrate molecule can be used to provide compounds of formula (I) that contain multiple hydroxyl groups in $R^2$.

Formulation and Use of the Lipids for Transfection

The lipids described above may be formulated by various methods to be used in transfection. One of the simplest methods for formulation is reverse evaporation. In this procedure the required amount of the cationic lipid and a co-lipid (if used, e.g. a neutral lipid) are transferred into a round bottom flask. An amount of chloroform that is enough to dissolve the lipids is added, followed with enough molecular biology grade water to make the desired concentration of total lipids/volume (e.g. 2 mg/ml). The solution is evaporated in vacuo (e.g. on a rotary evaporator) and the chloroform removed under vacuum. As the chloroform is removed liposomes are formed in the aqueous medium. Other methods for formulation that can be used are sonication and microfluidization. In both cases the required amount of the cationic lipid and the co-lipid are transferred into a flask and an amount of chloroform that will dissolve the lipids to homogenous solution is added. The chloroform is evaporated to leave a thin film of lipid mixture in the flask. The lipid film is then hydrated with molecular biology grade water to make the desired concentration and sonicated or microfluidized.

Advantageously, the new lipids are formulated with one or more colipids, most advantageously neutral colipids, although the skilled artisan will recognize that other lipids, including cationic lipids, may be used. For example, formulations where the molar ratio of cationic lipid:DOPE was varied from 2:1 to 1:16 were prepared using the above methods. Compounds having the structure 7 above were prepared where the hydrocarbon chain was varied from $C_{10}$-$C_{20}$ and the histidine and lysine analogs 8 and 9 where the hydrocarbon chain was varied from $C_{10}$-$C_{20}$ were formulated in the same manner.

The new lipids may be formulated with one ore more cationic lipids and/or one or more neutral lipids. The neutral lipid(s) may be, for example, DOPE, DPhPE, cholesterol, DOPC, Lyso-PE (1-acyl-2-hydroxy-sn-glycero-3-phosphoethanolamine), Lyso-PC (1-acyl-3-hydroxy-sn-glycero-3-phosphocholine), and/or 3-alkyloxy-2-hydroxy-1-acetamidopropane.

The cationic lipid may be selected from the group consisting of DOTMA, DOTAP, DMRIE, DC-Chol, DDAB, DOSPA, DOSPER, DOGS, TMTPS, TMTOS, TMTLS, TMTMS, TMDOS, N-1-dimethyl-N-1-(2,3-diaoleoyloxypropyl)-2-hydroxypropane-1,3-diamine, N-1-dimethyl-N-1-(2,3-diamyristyloxypropyl)-2-hydroxypropane-1,3-diamine, N-1-dimethyl-N-1-(2,3-diapalmityloxypropyl)-2-hydroxypropane-1,3-diamine, N-1-dimethyl-N-1-(2,3-diaoleoyloxypropyl)-2-(3-amino-2-hydroxypropyloxy)propane-1,3-diamine, N-1-dimethyl-N-1-(2,3-diamyristyloxypropyl)-2-(3-amino-2-hydroxypropyloxy)propane-1,3-diamine, N-1-dimethyl-N-1-(2,3-diapalmityloxypropyl)-2-(3-amino-2-hydroxypropyloxy)propane-1,3-diamine, L-spermine-5-carboxyl-3-(DL-1,2-dipalmitoyl-dimethylaminopropyl-β-hydroxyethylamine, 3,5-(N,N-di-lysyl)-diaminobenzoyl-glycyl-3-(DL-1,2-dipalmitoyl-dimethylaminopropyl-(3-hydroxyethylamine), L-Lysine-bis(O,O'-oleoyl-β-hydroxyethyl)amide dihydrochloride, L-Lysine-bis-(O,O'-palmitoyl-β-hydroxyethyl)amide dihydrochloride, 1,4-bis[(3-(3-aminopropyl)-alkylamino)-2-hydroxypropyl)piperazine, L-Lysine-bis-(O,O'-myristoyl-β-hydroxyethyl)amide dihydrochloride, L-Ornithine-bis-(O,O'-myristoyl-β-hydroxyethyl)amide dihydrochloride, L-Ornithine-bis-(O,O'-oleoyl-β-hydroxyethyl)amide dihydrochloride, 1,4-bis[(3-(3-aminopropyl)-oleylamino)-2-hydroxypropyl]piperazine, L-Ornithine-bis-(O,O'-palmitoyl-β-hydroxyethyl)amide dihydrochloride, 1,4,-bis[(3-amino-2-hydroxypropyl)-oleylamino]-butane-2,3-diol, 1,4,-bis[(3-amino-2-hydroxypropyl)-palmitylamino]-butane-2,3-diol, 1,4,-bis[(3-amino-2-hydroxypropyl)-myristylamino]-butane-2,3-diol, 1,4-bis[(3-oleylamino)propyl]piperazine, L-Arginine-bis-(O,O'-oleoyl-β-hydroxyethyl)amide dihydrochloride, bis[(3-(3-aminopropyl)-myristylamino)2-hydroxypropyl]piperazine, L-Arginine-bis-(O,O'-palmitoyl-β-hydroxyethyl)amide dihydrochloride, L-Serine-bis-(O,O'-oleoyl-β-hydroxyethyl)amide dihydrochloride, 1,4-bis[(3-(3-aminopropyl)-palmitylamino)-2-hydroxypropyl]piperazine, Glycine-bis-(O,O'-palmitoyl-β-hydroxyethyl)amide dihydrochloride, Sarcosine-bis-(O,O'-palmitoyl-β-hydroxyethyl)amide dihydrochloride, L-Histidine-bis-(O,O'-palmitoyl-β-hydroxyethyl)amide dihydrochloride, cholesteryl-3β-carboxyl-amidoethylenetrimethylammonium iodide, 1,4-bis[(3-myristylamino)propyl]piperazine, 1-dimethylamino-3-trimethylammonio-DL-2-propyl-cholesteryl carboxylate iodide, cholesteryl-3β-carboxyamidoethyleneamine, cholesteryl-3β-oxysuccinamidoethylenetrimethylammonium iodide, 1-dimethylamino-3-trimethylammonio-DL-2-propyl-cholesteryl-3β-oxysuccinate iodide, 2-[(2-trimethylammonio)-ethylmethylamino]ethyl-cholesteryl-3β-oxysuccinate iodide, 3β[N—(N', N'-dimethylaminoethane)carbamoyl]cholesterol, and 3O[N-(polyethyleneimine)-carbamoyl]cholesterol, 1,4-bis[(3-palmitylamino)propyl]piperazine, L-Ornithylglycyl-N-(1-heptadecyloctadecyl)glycinamide, $N^2$,$N^5$-Bis(3-aminopropyl)-L-ornithylglycyl-N-(1-heptadecyloctadecyl)glycinamide, 1,4-bis[(3-(3-amino-2-hydroxypropyl)-alkylamino)-2-hydroxypropyl]piperazine $N^2$—[$N^2$,$N^5$-Bis(3-aminopropyl)-L-ornithyl]-N,N-dioctadecyl-L-glutamine, $N^2$—[$N^2$,$N^5$-Bis(aminopropyl)-L-ornithyl]-N—N-dioctadecyl-L-α-glutamine, 1,4-bis[(3-(3-amino-2-hydroxypropyl)-oleylamino)2-hydroxypropyl]piperazine, $N^2$—[$N^2$,$N^5$-Bis(aminopropyl)-L-ornithyl]-N—N-dioctadecyl-L-α-asparagine, N—[$N^2$—[$N^2$,$N^5$-Bis[(1,1-dimethylethoxy)carbonyl]-$N^2$,$N^5$-bis[3-[(1,1-dimethylethoxy)carbonyl]aminopropyl]-L-ornithyl-N—N-dioctadecyl-L-glutaminyl]-L-glutamic acid, $N^2$—[$N^2$,$N^5$-Bis(3-aminopropyl)-L-ornithyl]-N,N-diolyl-L-glutamine, $N^2$—[$N^2$,$N^5$-Bis(aminopropyl)-L-ornithyl]-N—N-dioleyl-L-α-glutamine, 4-bis[(3-(3-amino-2-hydroxypropyl)-myristylamino)-2-hydroxypropyl]piperazine, $N^2$—[$N^2$,$N^5$-Bis(aminopropyl)-L-ornithyl]-N—N-diolyl-L-α-asparagine, N—[$N^2$—[$N^2$,$N^5$-Bis[(1,1-dimethylethoxy)carbonyl]-$N^2$,$N^5$-bis[3-[(1,1-dimethylethoxy)carbonyl]aminopropyl]-L-ornithyl-N—N-dioleyl-L-glutaminyl]-L-glutamic acid, 1,4-bis[(3-(3-aminopropyl)-oleylamino)propyl]piperazine, $N^2$—[$N^2$,$N^5$-Bis(3-aminopropyl)-L- ornithyl]-N,N-dipalmityl-L-glutamine, $N^2$—[$N^2,N^5$-Bis(aminopropyl)-L-ornithyl]-N—N-dipalmityl-L-α-glutamine, $N^2$—[$N^2,N^5$-Bis(aminopropyl)-L-ornithyl]-N—N-dipalmityl-L-α-asparagine, N—[$N^2$—[$N^2,N^5$-Bis[(1,1-dimethylethoxy)carbonyl]-$N^2,N^5$-bis[3-[(1,1-dimethylethoxy)carbonyl]aminopropyl]-L-ornithyl-N—N-dipalmityl-L-glutaminyl]-L-glutamic acid, $N^2$—[$N^2,N^5$-Bis(3-aminopropyl)-L-ornithyl]-N,N-dimyristyl-L-glutamine, $N^2$—[$N^2,N^5$-Bis(aminopropyl)-L-ornithyl]-N—N-dimyristyl-L-α-glutamine, $N^2$—[$N^2,N^5$-Bis(aminopropyl)-L-ornithyl]-N—N-dimyristyl-L-α-asparagine, 1,4-bis[(3-(3-amino-2-hydroxypropyl)-palmitylamino)-2-hydroxypropyl]piperazine, N—[$N^2$—[$N^2,N^5$-Bis[(1,1-dimethylethoxy)carbonyl]-$N^2,N^5$-bis[3-[(1,1-dimethylethoxy)carbonyl]aminopropyl]-L-ornithyl-N—N-dimyristyl-L-glutaminyl]-L-glutamic acid, 1,4-bis[(3-(3-aminopropyl)-myristylamino)propyl]piperazine, $N^2$—[$N^2,N^5$-Bis(3-aminopropyl)-L-ornithyl]-N,N-dilaureyl-L-glutamine, $N^2$—[$N^2,N^5$-Bis(aminopropyl)-L-ornithyl]-N—N-dilaureyl-L-α-glutamine, $N^2$—[$N^2,N^5$-Bis(aminopropyl)-L-ornithyl]-N—N-dilaureyl-L-α-asparagine, N—[$N^2$—[$N^2,N^5$-Bis[(1,1-dimethylethoxy)carbonyl]-$N^2,N^5$-bis[3-[(1,1-dimethylethoxy)carbonyl]aminopropyl]-L-ornithyl-N—N-dilaureyl-L-glutaminyl]-L-glutamic acid, 3-[N',N'''-bis(2-tertbutyloxycarbonylaminoethyl)guanidino]-N,N-dioctadec-9-enylpropionamide, 3-[N',N'''-bis(2-tertbutyloxycarbonylaminoethyl)guanidino]-N,N-dipalmitylpropionamide, 3-[N',N'''-bis(2-tertbutyloxycarbonylaminoethyl)guanidino]-N,N-dimyristylpropionamide, 1,4-bis[(3-(3-aminopropyl)-palmitylamino)propyl]piperazine, 1,4-bis[(3-(3-amino-2-hydroxypropyl)-oleylamino)propyl]piperazine, N,N-(2-hydroxy-3-aminopropyl)-N-2-hydroxypropyl-3-N,N-diolylaminopropane, N,N-(2-hydroxy-3-aminopropyl)-N-2-hydroxypropyl-3-N,N-dipalmitylaminopropane, N,N-(2-hydroxy-3-aminopropyl)-N-2-hydroxypropyl-3-N,N-dimyristylaminopropane, 1,4-bis[(3-(3-amino-2-hydoxypropyl)-myristylamino)propyl]piperazine, [(3-aminopropyl)-bis-(2-tetradecyloxyethyl)]methyl ammonium bromide, [(3-aminopropyl)-bis-(2-oleyloxyethyl)]methyl ammonium bromide, [(3-aminopropyl)-bis-(2-palmityloxyethyl)]methyl ammonium bromide, Oleoyl-2-hydroxy-3-N,N-dimethyamino propane, 2-didecanoyl-1-N,N-dimethylaminopropane, palmitoyl-2-hydroxy-3-N,N-dimethyamino propane, 1,2-dipalmitoyl-1-N,N-dimethylaminopropane, myristoyl-2-hydroxy-3-N,N-dimethyamino propane, 1,2-dimyristoyl-1-N,N-dimethylaminopropane, (3-Amino-propyl)→4-(3-aminopropylamino)-4-tetradecylcarbamoyl-butylcarbamic acid cholesteryl ester, (3-Amino-propyl)→4-(3-amino-propylamino-4-carbamoylbutylcarbamic acid cholesteryl ester, (3-Amino-propyl)→4-(3-amino-propylamino)-4-(2-dimethylamino-ethylcarbamoyl)-butylcarbamic acid cholesteryl ester, Spermine-5-carboxyglycine (N'-stearyl-N'-oleyl) amide tetratrifluoroacetic acid salt, Spermine-5-carboxyglycine (N'-stearyl-N'-elaidyl) amide tetratrifluoroacetic acid salt, Agmatinyl carboxycholesterol acetic acid salt, Spermine-5-carboxy-[3-alanine cholesteryl ester tetratrifluoroacetic acid salt, 2,6-Diaminohexanoeyl β-alanine cholesteryl ester bistrifluoroacetic acid salt, 2,4-Diaminobutyroyl β-alanine cholesteryl ester bistrifluoroacetic acid salt, N,N-Bis (3-aminopropyl)-3-aminopropionyl β-alanine cholesteryl ester tristrifluoroacetic acid salt, [N,N-Bis(2-hydroxyethyl)-2-aminoethyl]aminocarboxy cholesteryl ester, Stearyl carnitine ester, Palmityl carnitine ester, Myristyl carnitine ester, Stearyl stearoyl carnitine ester chloride salt, L-Stearyl Stearoyl Carnitine Ester, Stearyl oleoyl carnitine ester chloride, Palmityl palmitoyl carnitine ester chloride, Myristyl myristoyl carnitine ester chloride, L-Myristyl myristoyl carnitine ester chloride, 1,4-bis[(3-(3-amino-2-hydroxypropyl)-palmitylamino)propyl]piperazine, N-(3-aminopropyl)-N,N-bis-(dodecyloxyethyl)-piperazinium bromide, N-(3-aminopropyl)-N,N-bis-(oleyloxyethyl)-piperazinium bromide, N-(3-aminopropyl)-N,N-bis-(palmityloxyethyl)-piperazinium bromide, N-(3-aminopropyl)-N,N'-bis-(myristyloxyethyl)-piperazinium bromide, N-(3-aminopropyl)-N'-methyl-N,N'-(bis-2-dodecyloxyethyl)-piperazinium bromide, N-(3-aminopropyl)-N'-methyl-N,N'-(bis-2-oleyloxyethyl)-piperazinium bromide, N-(3-aminopropyl)-N'-methyl-N,N'-(bis-2-palmityloxyethyl)-piperazinium bromide, N-(3-aminopropyl)-N'-methyl-N,N'-(bis-2-myristyloxyethyl)-piperazinium bromide, 1,4-bis[(3-(3-aminopropyl)-oleylamino)-2-hydroxy-propyl]piperazine, 1,4-bis[(3-(3-aminopropyl)-myristylamino)-2-hydroxy-propyl]piperazine, and 1,4-bis[(3-(3-aminopropyl)-palmitylamino)-2-hydroxy-propyl]piperazine.

Other formulations may also include one or more polyamine transfection agents, such as dense star dendrimers, PAMAM dendrimers, $NH_3$ core dendrimers, ethylenediamine core dendrimers, dendrimers of generation 5 or higher, dendrimers with substituted groups, dendrimers comprising one or more amino acids, grafted dendrimers, activated dendrimers, polyethylenimine, and/or polyethylenimine conjugates.

Still other formulations may include transfection enhancing agents such as a fusion agent, a cell surface ligand and/or a nuclear localization agent such as a nuclear receptor ligand peptide, Examples of transfection enhancing agents include, but are not limited to, reovirus-related fusogenic peptides (see WO07/130073, which is hereby incorporated by reference in its entirety), insulin, a transferrin, epidermal growth factor, fibroblast growth factor, a cell targeting antibody, a lactoferrin, a fibronectin, an adenovirus penton base, Knob, a hexon protein, a vesicular stomatitis virus glycoprotein, a Semliki Forest Virus core protein, a influenza hemagglutinin, a hepatitis B core protein, an HIV Tat protein, a herpes simplex virus VP22 protein, a histone protein, a arginine rich cell permeability protein, a high mobility group protein, and invasin protein, and internalin protein, an endotoxin, a diphtheria toxin, a shigella toxin, a melittin, a magainin, a gramicidin, a cecrophin, a defensin, a protegrin, a tachyplesin, a thionin, a indolicidin, a bactenecin, a drosomycin, an apidaecin, a cathelicidin, a bactericidal-permeability-increasing protein, a nisin, a buforin, and fragments thereof.

Use of these compositions in transfection can be carried out by methods that are known in the art. See for example, WO07/130073, at pages 54-60 which describes "before" and "after" protocols for transfection where the components of a transfection complex are mixed in differing orders prior to addition to a cell culture. Typically, a liposomal preparation of the lipid, with or without colipid is prepared, and is then mixed with a macromolecule, such as a DNA molecule or RNAi molecule to form a transfection complex. The complex is then added to a cell culture and transfection is monitored using well known methods. Additional components such as cell surface ligands, fusion agents, nuclear localization agents and the like may be added to the nucleic acid prior to admixture with the liposome, or may be added to the liposome prior to addition of nucleic acid.

Cells which can be transfected according to these methods include, but are not limited to, virtually any eukaryotic cell including primary cells, cells in culture, a passaged cell culture or a cell line, and cells in cultured tissue. Suitable cells include human cell lines and animal cell lines. The cell may be a fibroblast. The cells can be attached cells or cells in suspension (suspension cells). In certain illustrative aspects, the cells are suspension CHO—S cells and suspension 293-F cells. Other cells that may be used include, without limitation, 293, 293-S, CHO, Cos, 3T3, Hela, primary fibroblasts, A549, Be2C, SW480, CHOK1, Griptite 293, HepG2, Jurkat, LNCap, MCF-7, NIH-3T3, PCl2, C6, Caco-2, COS-7, HL60, HT-1080, IMR-90, K-562, SK-BR3, PHP1, HUVEC, MJ90, NHFF, NDFF and primary neurons.

In another embodiment is a method for producing a protein which includes contacting a cell with a lipid-nucleic acid complex as described above, where the nucleic acid encodes the protein. The cells are incubated to produce the protein and the protein is collected. Cells which can be used for protein production are described above. In addition, any composition which includes a lipid of Formula (I) or (II) can be used for transfection of cells. Such compositions are further discussed herein, and include, but are not limited to compositions comprising lipids of Formula (I) or (II), a co-lipid and an optional transfection enhancing agent such as a fusogenic peptide or protein.

In another embodiment is a method for inhibiting production of a protein in a cell, comprising contacting the cell with a lipid-nucleic acid complex as described above, where the nucleic acid is a double stranded RNA molecule, such as an RNAi or siRNA molecule designed to inhibit expression of the protein. Methods of designing such RNA molecules are well known in the art. Lipids of Formula (I) are particularly suitable for deliver of RNAi molecules in this fashion. The cells are incubated and the phenotypic consequence of inhibiting production of the selected protein is observed. The lipids formulated in this manner were used in transfection. The transfection of 293, CHO-K1, NIH3T3, Hela A549, Umbilical Cord Mesenchymal Stem Cells (UB Stem), Adipose Mesenchymal Stem Cells(HMSC-Ad) and Neonatal Human Fibroblast (Nuff) with β-galactosidase reporter plasmid pCMV.SPORT-β-gal was carried out using the formulation VII-97-G which contains the histidine analog of Compound 6. The result is shown in the figure below (FIG. 1)

Reagent Kits

Components of the transfection compositions described above can be provided in a reagent kit. The kits contain the lipid of formula (I) or (II) above, together with additional components, such as a neutral lipid, a cationic lipid, cell surface ligands, fusion agents, and/or nuclear localization agents and the like. The kit components may be separate or may be premixed in any manner. For example, the lipid of formula (I) or (II) may be admixed with one or more neutral lipid. Additional components may also be present in the same container or may be present in one or more separate containers. The kits typically include vessels, such as vials and/or tubes, which are packaged together, for example in a cardboard box. The kits can be shipped from a supplier to a customer. For example, in one example provided herein is a kit that includes a vial that includes a liposomal formulation as described above and, optionally, a transfection agent and a transfection enhancing peptide. The kit can also include, for example, a separate vessel that includes a transfection enhancing agent, such as a transfection enhancing peptide, for example Plus Reagent™ (Invitrogen Corp., Carlsbad, Calif.). The kit can also include in separate containers, cells, cell culture medium, and a reporter nucleic acid sequence, such as a plasmid that expresses a reporter gene. In certain examples, the culture medium can be reduced-serum medium and/or protein expression medium.

Also provided are kits containing a compound of Formula (I) or(II) and additional reagents such as a cationic lipid, a neutral lipid, an amphipathic peptide, an amphipathic peptide comprising a polycationic nucleic acid binding moiety, a cell surface ligand, a cell surface ligand comprising a polycationic nucleic acid binding moiety, a fusion agent, a fusion agent comprising a polycationic nucleic acid binding moiety, a nuclear localization peptide or protein, and a nuclear localization peptide or protein comprising a polycationic nucleic acid binding moiety. The kits may contain one, some, or all of these additional reagents, in any possible combination. Advantageously, the additional reagents include a cationic lipid, an amphipathic peptide and a cell surface ligand that contains a polycationic nucleic acid binding moiety. When the cell surface ligand is a peptide or protein, the polycationic nucleic acid binding moiety is a polybasic amino acid sequence.

In one embodiment, a kit comprises individual portions of, or a mixture of, cationic lipid, such as a lipid of Formula (I), and peptide, protein or fragment thereof or modified peptide, protein or fragment thereof. In another embodiment, a kit comprises individual portions of, or a mixture of, polycationic polymers and peptide, protein or fragments thereof or modified peptide, protein or fragments thereof. Cationic lipid transfection kits can optionally include neutral lipid as well as other transfection-enhancing agents or other additives, and the relative amounts of components in the kit may be adjusted to facilitate preparation of transfection compositions. Kit components can include appropriate medium or solvents for other kit components.

Nucleic acids that can be transfected by the methods of this invention include DNA and RNA (including RNAi/siRNA) of any size from any source comprising natural bases or non-natural bases, and include those encoding and capable of expressing therapeutic or otherwise useful proteins in cells, those which inhibit undesired expression of nucleic acids in cells, those which inhibit undesired enzymatic activity or activate desired enzymes, those which catalyze reactions (ribozymes), and those which function in diagnostic assays (e.g., diagnostic nucleic acids). Therapeutic nucleic acids include those nucleic acids that encode or can express therapeutically useful proteins, peptides or polypeptides in cells, those which inhibit undesired expression of nucleic acids in cells, and those which inhibit undesired enzymatic activity or activate desired enzymes in cells.

The compositions and methods provided herein can also be readily adapted in view of the disclosure herein to introduce biologically-active macromolecules other than nucleic acids including, among others, polyamines, polyamine acids, polypeptides and proteins into eukaryotic cells. Other materials useful, for example as therapeutic agents, diagnostic materials, research reagents, which can be bound to the peptides and modified peptides and introduced into eukaryotic cells by the methods of this invention.

The present invention, thus generally described, will be understood more readily by reference to the following examples, which are provided by way of illustration and are not intended to be limiting of the present invention.

EXAMPLES

Example 1: Synthesis of Compounds 7-9

Dimethyl tartrate (1)(7.12 g) was combined with 50 ml of methylamine solution in THF (2M) in a high pressure reactor tube. The tube was heated at 70° C. overnight (22 hrs). The reaction mix was cooled to room temperature and kept at 4° C. for about 1 hour. The precipitate was filtered and washed twice with 50 ml of THF to obtain compound (2, $R^2$=Me) as a white solid material.

NaH (1 g; 60% oil dispersion) was triturated twice with hexane (10 ml). Dimethylaminotartaramide (2)(1.78 g) was added followed by THF (500 ml). The reaction mix was heated under reflux overnight, after which oleyl mesylate was dissolved in 50 ml THF and added to the reaction mix. The reaction mix was heated under reflux for 3-5 days. The reaction was stopped when TLC analysis (silica gel, ethyl acetate hexane 1:1) indicated that there was no change in the pattern of reaction products. The reaction mixture was cooled and water (400 ml) was added. The organic (top) layer was separated and concentrated in vacuo on a rotary evaporator. The resulting material was dissolved in 5 ml ethyl acetate and applied to a flash silica column (100 g) that was equilibrated with 1% ethyl acetate in hexane. The column was eluted with 1 L each of 1% ethyl acetate in hexane, ethyl acetate/hexane (3:7), ethyl acetate/hexane (4:6), ethyl acetate hexane (1:1) and 50 ml fractions were collected. The fractions that contained the desired material, Compound (3, $R^1$=oleyl), were combined and concentrated. The material was characterized by TLC and ESMS ($MH^+$ 677)

Compound (3) (0.7 g) was suspended in 100 ml anhydrous THF and 10 ml of 1 M lithium aluminum hydride solution in THF was added drop-wise. After the addition was completed, the reaction mix was refluxed overnight. The mixture was cooled to room temperature and 0.5 ml of water was added very carefully followed by 0.5 ml 15% NaOH and 1.5 ml of water. The reaction mixture was stirred magnetically and the THF was decanted while the mixture was still hot. The THF was removed in vacuo on a rotary evaporator and the residue was dissolved in 400 ml chloroform and extracted with water (2×300 ml). The solution was concentrated and the resulting gum was dissolved in 5 ml chloroform and applied to a flash silica column (100 g) that was equilibrated with 1% methanol in chloroform. The column was eluted with 1 L each of 1%, 5%, 10%, 20% and 30% methanol in chloroform. The fractions that contained the desired material, Compound (4, $R^1$=oleyl, $R^2$=methyl), were combined. It was characterized by TLC and ESMS ($MI-1^+$649).

BOC-protected carboxy-spermine (210 mg) was dissolved in 2 ml DMF/$CH_2Cl_2$. N-hydroxysuccinimide (36 mg) and diisopropylcarbodiimide (0.041 ml) were added to the solution and the mix was stirred for 2 hrs. Compound (4) in 1 ml $CH_2Cl_2$ was added to the reaction mix and stirring continued at room temperature overnight. The reaction mix was diluted with 100 ml $CH_2Cl_2$ and the solution was extracted with water (2×100 ml). The organic layer was separated and concentrated and taken up into 5 ml chloroform and loaded on a silica flash column (50 g) that previously was equilibrated with 1% methanol in chloroform. The column was eluted with 800 ml each of 1% and 3% methanol in chloroform. The fractions that contain the desired material, BOC-protected Compound 5, were combined and concentrated. The material was taken up into 2 ml methylene chloride and treated with 2 ml of trifluoroacetic acid for 1 hr. The mix was concentrated and co evaporated with ethanol (2×50 ml) to obtain Compound (7, $R^1$=oleyl, $R^2$=methyl) as a gum. It was characterized by TLC and ESMS ($MH^{2+}$ 553.8)

To prepare compound (8, $R^1$=oleyl, $R^2$=methyl), BOC His(BOC)—NHS (332 mg) and diisopropylethylamine were dissolved in 10 ml $CH_2Cl_2$. The diamine, Compound (4, $R^1$=oleyl, $R^2$=methyl), in 2 ml $CH_2Cl_2$ was added in one portion to the NHS ester solution and stirred overnight. TLC analysis on silica showed the disappearance of starting material ($CHCl_3$:MeOH 90:10) and formation of product ($CHCl_3$:MeOH 95:5). The reaction mix was diluted with 200 ml $CH_2Cl_2$ and extracted with 200 ml of water followed by 200 ml of saturated $NaHCO_3$ solution. The organic layer was separated and concentrated and the residue dissolved in 5 ml chloroform and loaded on a flash column (50 g) equilibrated with chloroform (0.8% ethanol). The column was eluted with 1 L each of chloroform and 1% MeOH in chloroform. Fractions that contain the desired material, BOC protected Compound (8), were combined and concentrated. The gummy intermediate was characterized by TLC and ESMS ($MH^+$ 1323). The material was dissolved in 4 ml $CH_2Cl_2$ and 2 ml of trifluoroacetic acid was added and mixture incubated at room temperature for 2 hrs. The reaction mix was concentrated and co-evaporated with methylene chloride (2×50 ml) and methanol (1×50 ml) to obtain the trifluoroacetate salt of Compound (8, $R^1$=oleyl, $R^2$=methyl). It was characterized to be Compound 8 by TLC (Silica, $CHCl_3$:MeOH:$H_2O$:$NH_4OH$ 60:20:1:1) and ESMS ($MH^+$ 923).

Example 2: Formulation of Cationic Lipids into Liposomes

The liposome was formulated using reverse evaporation. Thus, 6.32 mg of the TFA salt of Compound (8, $R^1$=oleyl, $R^2$=methyl) and 13.67 mg of DOPE (1:4 molar ration of TFA salt of Compound 8:DOPE) were combined and placed in a round bottom flask. The lipid mixture was dissolved in 2 ml of chloroform. 10 ml of water was added to the chloroform solution. The chloroform was removed under vacuum on a rotary evaporator to obtain a liposome solution. The solution was adjusted to 10 ml to obtain a 2 mg/ml liposome solution. It was designated as VII-97-G. Formulations where the molar ratios varied from 2:1 to 1:16 (TFA salt of Compound (8, $R^1$=oleyl, $R^2$=methyl):DOPE) were prepared in this manner.

Example 3: Transfection Protocol

Transfection of 8 different cell types with β-galactosidase reporter plasmid pCMV.SPORT-β-gal was carried out as follows:

Cells were plated in 96-well plates with 100 μl of media containing 5-10% fetal calf serum the day prior to transfection such that a desired confluency (70%-95%) was achieved. The following day a transfection agent that included a liposomal composition of the lipid VII-97-G and DNA were mixed in Opti-MEM to form DNA/lipid complexes. Complexes were formed by adding various amounts of lipids (1 μl to 6 μl to 50 μl of Opti-MEM) DNA (100 ng) was added to 50 μl Opti-MEM. The DNA and lipid solutions were then mixed to form DNA lipid complexes. The complexes were incubated for at least 20 minutes after which 10 μl DNA/lipid complexes were added to cells. Lipofectin and Lipofectamine (Invitrogen, Carlsbad, Calif.) were used as described by the manufacturer.

Cells were incubated for an additional 24 hours to allow expression of the plasmid. Medium was removed and the cells were lysed in 100-200 μl of lysis buffer. The lysates (20 μl) were assayed for β-gal activity using the enzymatic substrate ONPG. Total activity was determined by reading the OD at 405 using Bio-Rad Benchmark Microplate Spectrophotometer.

FIGS. 1-4 show the results obtained, and compare those results to two widely used commercial reagents. The results show that the lipids described above provided significantly enhanced transfection efficiency, as measure by β-gal expression, across all cell types.

Compounds having the structures shown below, where R is $C_{14}$, $C_{16}$, or $C_{18}$ alkyl, or $C_{14}$, $C_{16}$, or $C_{18}$ monounsaturated alkenyl, were prepared and shown to be effective for transfection of nucleic acids as described above.

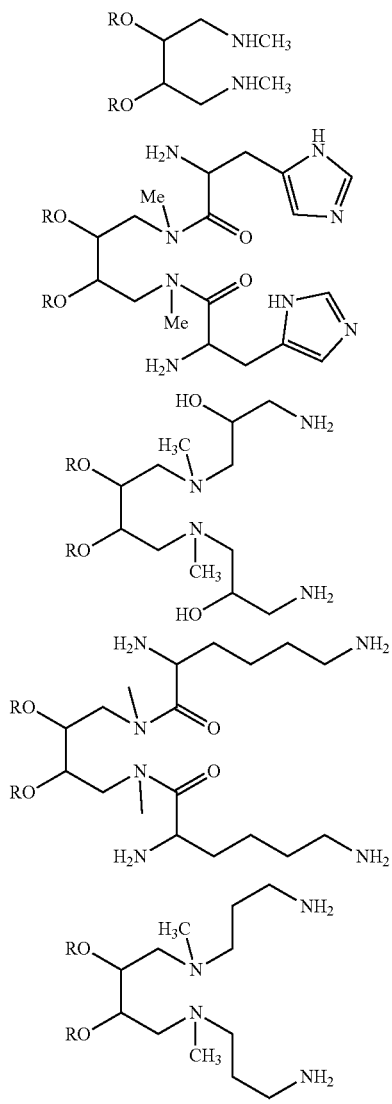

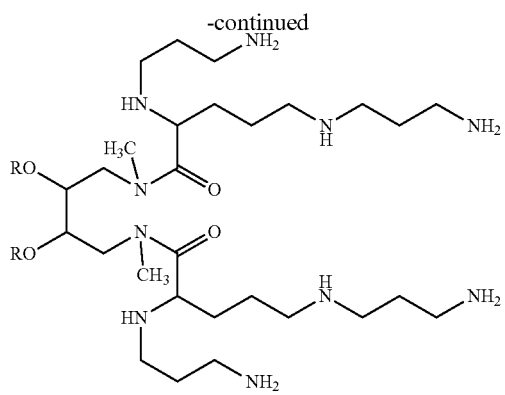

Example 4: RNAi Transfection Protocol

Plates were seeded such that a confluency of approximately 20% was reached at the time of transfection (~24 hours post-plating).

Transfection complexes were formed by combining the appropriate transfection reagent containing a lipid of formula (I) (1, 2, 3, 4, 5, and 6 μl) and either GAPDH-silencing or negative control RNA (25 nM final) in 200 μl of Opti-Mem™. Complexes were allowed to form for 20 minutes at room temperature.

After the 20 minute complexing reaction, 20 μl of each reagent/RNA mixture was transferred to the appropriate well containing the adherent cells and 100 μl of complete culture medium (including serum). Incubation was carried out for 72 hours at 37° C. and 5% $CO_2$. After this 72 hour incubation period, plates were harvested by aspirating the medium from the wells, followed by 2 washes of 100 μl per well with PBS (with calcium and magnesium), aspirating off the PBS each time. Plates were then frozen at −80° for 30 to 60 minutes.

After warming plates to room temperature, 100 μl of lysis buffer was added to each well and cells are lysed by vigorous mixing. Following lysis, 20 μl of extract was transferred to fresh plates and the GAPDH activity was determined based on the coupled reduction of INT-Violet (iodonitrotetrazolium) as measured by an increase in absorbance at 492 nm.

Results

The following cell lines showed good knockdown of GAPDH enzyme activity, with low toxicity, when transfected with a compound of formula (II) where $R^1$=$C_{14}H_{27}$ $R^2$=$CH_2$—CHOH—$CH_2NH_2$, $R^{10}$=$CH_3$/DOPE (1:4) and an siRNA directed against GAPDH mRNA:

3T3
HDFa (human diploid fibroblast, adult)
HepG2

What is claimed is:

1. A composition comprising a compound having the structure

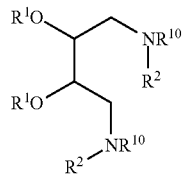

wherein each $R^1$ independently is $C_1$-$C_{23}$ alkyl, $C_1$-$C_{23}$ alkenyl, (CO)$C_1$-$C_{23}$ alkyl, or (CO)$C_1$-$C_{23}$ alkenyl; and each $R^2$ independently is —$CH_2$—$(CHR^3)_{1-6}$—$CH_2$—$NHR^4$ or —$CH_2$—$(CHR^3)_{0-6}$—$CH_2$—OH, wherein each $R^3$ independently is H, OH, or NH2,
$R^4$ is H or $CH_3$; and
$R^{10}$ is H or $C_1$-$C_8$ alkyl;
and an amphipathic peptide.

2. A composition according to claim 1, wherein said amphipathic peptide is selected from the group consisting of the peptides having sequences corresponding to SEQ ID NOs: 10-18.

3. A composition according to claim 1, wherein each $R^2$ independently is —$CH_2$—$(CHR^3)_{1-6}$—$CH_2$—$NHR^4$.

4. A composition according to claim 3, wherein each $R^3$ is H.

5. A composition according to claim 3, wherein each $R^4$ is H.

6. A composition according to claim 3, wherein each $R^{10}$ is H.

7. A composition according to claim 1, wherein each $R^2$ independently is —$CH_2$—$(CHR^3)_{0-6}$—$CH_2$—OH.

8. A composition according to claim 1, further comprising at least one cationic lipid.

9. A composition according to claim 1 further comprising at least one neutral lipid.

10. A composition according to claim 1 comprising a polyamine transfection agent.

11. A composition according to claim 1 further comprising a fusion agent.

12. A composition according to claim 1, further comprising a cell surface ligand, wherein said cell surface ligand optionally comprises a polycationic nucleic acid binding moiety.

13. A composition according to claim 1 comprising a nuclear localization peptide or protein, wherein said nuclear localization peptide or protein optionally comprises a polycationic nucleic acid binding moiety.

14. A composition according to claim 1, further comprising a nucleic acid.

15. A composition according to claim 14, wherein said nucleic acid comprises an RNA molecule.

16. A method of introducing a nucleic acid into a eukaryotic cell, comprising contacting the cell with the nucleic acid and a composition according to claim 1, thereby introducing the nucleic acid into the cell.

17. A method of expressing a protein in a cell, comprising contacting the cell with an expression vector encoding the protein and a composition according to claim 1.

18. A method of inhibiting expression of a protein in a cell, comprising contacting the cell with a composition according to claim 15.

* * * * *